(12) United States Patent
Yamasaki et al.

(10) Patent No.: US 6,525,023 B1
(45) Date of Patent: *Feb. 25, 2003

(54) VASCULAR SMOOTH MUSCLE CELL GROWTH FACTOR

(75) Inventors: Motoo Yamasaki, Machida (JP); Kenji Shibata, Tama (JP); Nobuo Hanai, Sagamihara (JP); Akiko Furuya, Machida (JP); Kaoru Miyamoto, Maebashi (JP)

(73) Assignee: Kyowa Hakko Kogyo Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/132,769

(22) Filed: Aug. 12, 1998

(30) Foreign Application Priority Data

Aug. 13, 1997 (JP) .................................. 9-218491

(51) Int. Cl.⁷ ...................... A61K 38/18; C07K 14/475
(52) U.S. Cl. .............................. 514/12; 514/2; 530/399
(58) Field of Search ................................ 530/350, 399; 514/2, 12

(56) References Cited

FOREIGN PATENT DOCUMENTS

| WO | WO 93/20196 A | | 10/1993 |
| WO | WO 93/20196 | * | 10/1993 |
| WO | WO 95/05191 | | 2/1995 |

OTHER PUBLICATIONS

Science, 235, 442–447 (1987).
Cell, 69, 95–110 (1992).
Proc. Natl. Acad. Sci. USA, 79, 5867–5870 (1982).
Endocrinology, 118, 82 (1986).
Proc. Natl. Acad. Sci. USA, 83, 9050–9054 (1986).
Proc. Natl. Acad. Sci. USA, 86, 9911–9915 (1989).
Klar, A. "F–Spondin: a gene expressed at high levels in the floor plate encodes a secreted protein that promotes neural cell adhesion and neurite extension", Cell, vol. 69, Apr. 3, 1992, PP 95–110.
Nucleotide sequence database EMBL, Id: HS929178; AC H37929 Jul. 27, 1995.
Nucleotide sequence database EMBL, Id: HS449155; AC H09449 Jul. 2, 1995.
Nucleotide sequence database EMBL, Id: HS79392; AC R25793 Apr. 29, 1995.
Nucleotide sequence database EMBL, Id: HD1249630; AC AA449547 Jun. 27, 1995.

* cited by examiner

Primary Examiner—Christine J. Saoud
(74) Attorney, Agent, or Firm—Antonelli, Terry, Stout & Kraus, LLP

(57) ABSTRACT

The present invention provides a novel vascular smooth muscle cell growth factor, a DNA encoding VSGF, a vector containing the DNA, a method for producing a transformant obtained by transformation with the vector, a method for producing VSGF, an antibody specifically reactive to the VSGF and a method for producing the antibody. The VSGF of the present invention is useful for diagnosis and therapy of wound healing failure, intractable skin ulcer, or abnormal blood vessel forming disease by fibroblast growth factor.

3 Claims, 8 Drawing Sheets

97 — 
68 —

40 —

30 —
20 —

VASCULAR SMOOTH MUSCLE CELL GROWTH FACTOR

BACKGROUND OF THE INVENTION

1. Field of the Invention

The present invention relates to a novel vascular smooth muscle cell growth factor (VSGF, hereinafter), a DNA encoding the VSGF, a vector comprising the DNA, a transformant obtained by transformation with the vector, and a method for producing the VSGF. Further, the present invention relates to an antibody specifically reacting with the VSGF and a method for producing the antibody. Furthermore, the present invention relates to a wound healing agent containing the VSGF and an agent against abnormal vascular formation.

2. Prior Art

As a factor having vascular smooth muscle cell growth promotion activity, there has been known a fibroblast growth factor [Endocrinology, 118, 82 (1986)], platelet-derived growth factor [Proc. Natl. Acad. Sci. USA, 79, 5867 (1982)], and thrombospondin [Proc. Natl. Acad. Sci. USA, 83, 9050 (198-6)]. Fibroblast growth factor has been known as a factor of abnormal vascular formation [(Proc. Natl, Acad. Sci. USA, 86, 9911 (1989)]. However, these factors have different properties from those of the factor of the present invention.

Although F-spondin has been known as a factor promoting adhesion and elongation of a nerve cell [(Cell, 69, 95 (1992)], an effect of F-spondin on growth of a vascular smooth muscle cell has not been known.

Vascular formation disorders include wound healing failure and intractable skin ulcer, for which no effective drugs are known. In addition, diseases of abnormal vascular formation include diabetic retinopathy, psoriasis, rheumatoid arthritis, angiomatosis, arteriosclerosis, and solid tumor [Science, 235, 442 (1987); Zikken Igaku 8, 369 (1990)]. Fibroblast growth factor has been suggested as related to these diseases. However, an agent for vascular formation disease and particularly, an agent for vascular formation disease caused by the fibroblast growth factor as one of the main factors of vascular formation has not been known.

Furthermore, an antibody specifically reacting to the vascular smooth muscle cell growth factor has not been known so far.

An object of the present invention is to provide a novel vascular smooth muscle cell growth factor promoting growth of vascular smooth muscle cell, a DNA encoding the VSGF, a vector comprising the DNA, a method for producing a transformant obtained by transformation with the vector, a method for producing the VSGF, an antibody specifically reacting to the VSGF and a method of immunological detection by using the antibody.

SUMMARY OF THE INVENTION

The present invention relates to a polypeptide obtained from a mammal and having vascular smooth muscle cell growth promotion activity. The mammal includes bovine and human but are not limited thereto. The present invention relates to a polypeptide having an amino acid sequence represented by SEQ ID NO: 1 or SEQ ID NO: 3, or a polypeptide having vascular smooth muscle cell growth promotion activity and having an amino acid sequence wherein one or more amino acid residues are substituted, deleted, or added in the amino acid sequence represented by SEQ ID NO: 1 or SEQ ID NO: 3, and also relates to a DNA encoding those polypeptides or a DNA having a nucleotide sequence represented by SEQ ID NO: 2 or SEQ ID NO: 4 or a DNA which is hybridizable with the DNA represented by SEQ ID NO:2 or 4 under stringent conditions and encodes a human-derived polypeptide having vascular smooth muscle cell growth promotion activity. Furthermore, the present invention relates to a recombinant vector comprising the VSGF DNA, a transformant obtained by introducing the recombinant vector into a host cell, and a method of producing a polypeptide comprising cultivating a transformant in a culture medium to form and accumulate a polypeptide of the present invention in a culture, and collecting the polypeptide therefrom.

The present invention provides an antibody specifically reacting with the polypeptide of the present invention, a method of producing the antibody, and a method of immunological detection of wound healing failure, intractable skin ulcer, diabetic retinopathy, psoriasis, rheumatoid arthritis, angiomatosis, arteriosclerosis, and solid tumor by using the VSGF antibody of the invention.

The present invention relates to an agent for healing wound or for preventing abnormal vascular formation, containing a polypeptide of the present invention or a polypeptide having an amino acid sequence represented by SEQ ID NO: 5.

BRIEF DESCRIPTION OF THE DRAWINGS

FIG. 1 shows absorbance of each fraction at purification of a bovine VSGF with DEAE Sepharose and FIG. 1B shows vascular smooth muscle cell growth promotion activity.

FIG. 8A is a diagram in the case of the administration of 100 ng of bFGF and FIG. 8B is a diagram in the case of 1 μg of recombinant human VSGF in addition to 100 ng of bFGF.

MODES FOR CARRYING OUT THE INVENTION

Figure 1:
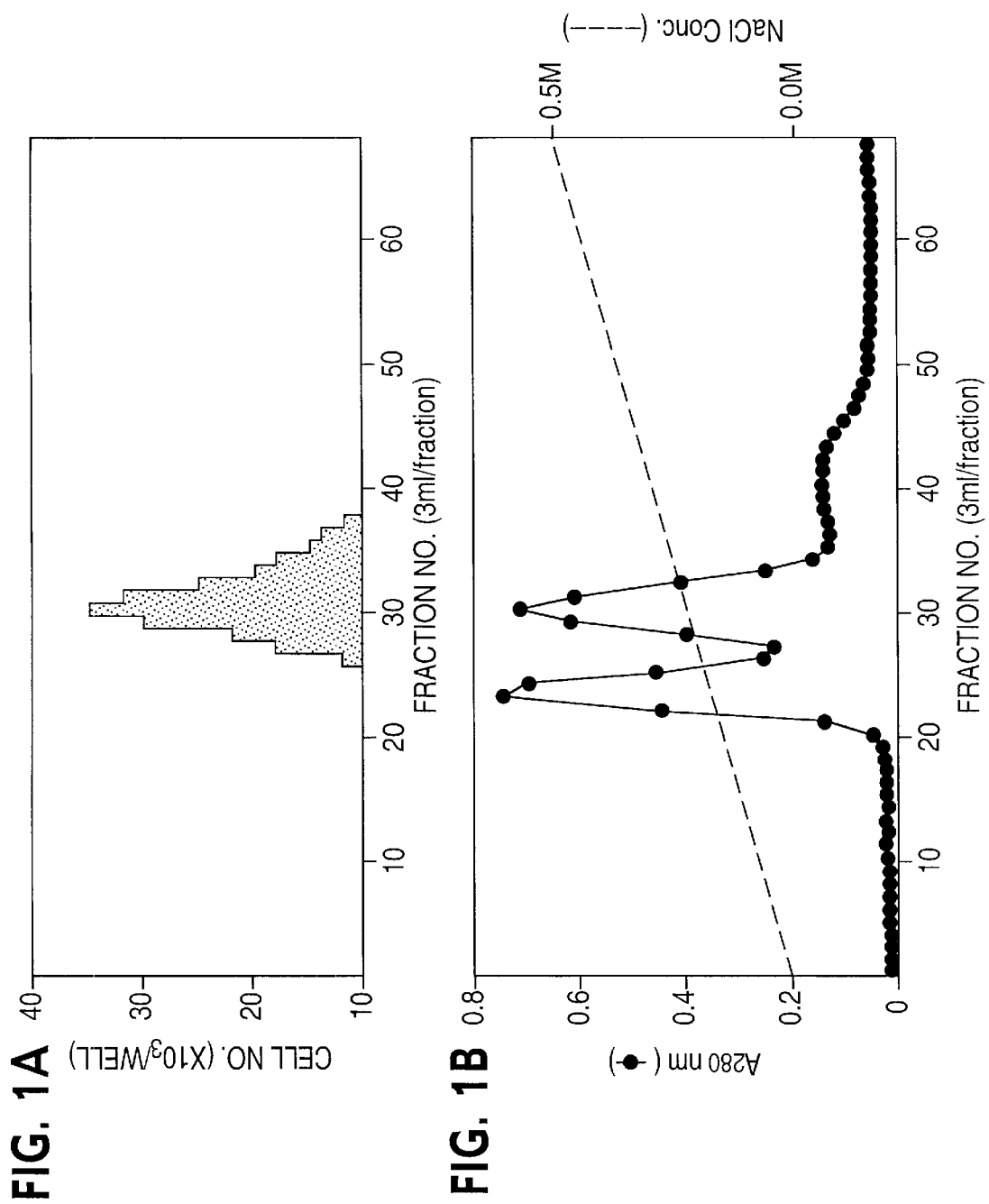

The inventor of the present invention successfully isolated and purified a novel VSGF, and cloned the VSGF DNA of the present invention by intensive research based on the objects mentioned above. In addition, the present inventors produced a transformant obtained by using an expression vector comprising a DNA encoding the VSGF of the present invention and produced the VSGF by employing the transformant, and finally resulted in completing the present invention.

A polypeptide of the present invention includes a polypeptide having an amino acid sequence represented by SEQ ID NO: 1, a polypeptide having an amino acid sequence represented by SEQ ID NO: 3, or a polypeptide having vascular smooth muscle cell growth promotion activity and having an amino acid sequence wherein one or more amino acid residues are substituted, deleted, or added in the amino acid sequence represented by SEQ ID NO: 1 or 3.

The substitution, deletion, or addition of amino acid resudues can be carried out by site specific mutation inducing method [Nucleic Acid Res., 10, 6487–6500 (1982)].

The measurement of vascular smooth muscle cell growth promotion activity is carried out by, for example, a method with an indication of cell number of smooth muscle cell of bovine artery; the method will be described in an Example of the present invention.

The DNA encoding the polypeptide of the present invention includes a DNA having a nucleotide sequence represented by SEQ ID NO: 2 or 4 and a DNA which is hybridizable with the DNA having a nucleotide sequence represented by SEQ ID NO: 2 or 4 under stringent condition and encoding a polypeptide having vascular smooth muscle cell growth promotion activity.

The DNA which hybridizes under stringent conditions with a DNA comprising a nucleotide sequence selected from the nucleotide sequences represented by SEQ ID NO: 2 or SEQ ID No:4 means a DNA which is obtained by colony hybridization, plaque hybridization, Southern blot hybridization or the like using, as a probe, a DNA comprising a nucleotide sequence selected from the nucleotide sequences represented by SEQ ID NO:2 or SEQ ID NO:4.

Examples include DNA which can be identified by carrying out hybridization at 65° C. in the presence of 0.7–1.0 M NaCl using a filter on which a DNA prepared from colonies or plaques is immobilized, and then washing the filter with 0.1 to 2×SSC solution (the composition of 1×SSC comprises 150 mM sodium chloride and 15 mM sodium citrate) at 65° C.

The hybridization can be carried out in accordance with known methods described in, for example, *Molecular cloning, A Laboratory manual,* Second Edition, Cold Spring Harbor Laboratory Press (1989) (referred to as *"Molecular Cloning,* 2nd ed." hereinafter), *Current Protocols in Molecular Biology,* John Wiley & Sons (1987–1997) (referred to as *"Current Protocols in Molecular Biology"* hereinafter), *DNA Cloning* 1: *Core Techniques, A Practical Approach,* Second Edition, Oxford University (1995) or the like. Specific examples of the DNA which can be hybridized include a DNA having a homology of 60% or more with a nucleotide sequence selected from the nucleotide sequences represented by SEQ ID NO:2 or 4, preferably a DNA having a homology of 80% or more, and more preferably a DNA having a homology of 95% or more.

The VSGF of the present invention is obtained by isolating VSGF from an organ or cell line of various animals including human, a method using a transformant obtained by introducing a vector having DNA encoding VSGF into a host cell, or by a method comprising the use of DNA recombination technique such as production by in vitro translation with a template that is a mRNA prepared by in vitro transcription by using the vector.

VSGF is isolated from the organ and cell line of an animal by separating and purifying protein from supernatant obtained by centrifuging animal tissue using a combination of conventional methods for separating and purifying protein, such as absorption chromatography, ion exchange chromatography, reversed phase chromatography, and sodium dodecyl sulfate-polyacrylamide gel electrophoresis (SDS-PAGE).

Any organs and cell lines of animals in which vascular tissue is forming and which is obtained sufficiently as material for experiment, can be used. To obtain a large quantity of such material, ovary and liquid ovarian folliculi derived from vetebrate animals in luteinization are recommended, since vascular is actively forming during luteinization in the reproductive cycle, and bovine ovary is particularly preferred.

DNA encoding the VSGF of the present invention can be prepared and expressed by the methods described in the Molecular Cloning, a Laboratory Manual, 2nd ed., Current Protocols in Molecular Biology (Supplements 1–34) edited by Ausubel, Brent, Kingston, Moore, Seidman, Smith, and Stuhl, published by Green Publishing Associates and Wiley-Interscience, 1987–1996 (hereinafter abbreviated as Current Protocols in Molecular Biology (Supplements 1–34)). The following are methods using recombinant DNA techniques, and the methods follow the literature mentioned above, unless otherwise indicated.

DNA encoding the VSGF is obtained by (1) extracting RNA from cells of a mammal in which VSGF is expressed, (2) synthesizing a cDNA from the extracted RNA, (3) constructing cDNA library by inserting the obtained cDNA into a cloning vector, and (4) by selecting a transformant comprising the cDNA encoding the VSGF as a target.

To prepare total RNA from an ovary or placenta of an animal such as a bovine or a human wherein VSGF is expressed, guanidine/cesium chloride method and guanidine thiocyanate method [Methods in Enzymology, 154, 3 (1987)], etc., may be used. To prepare mRNA from the total RNA, column method or batch method using oligo-dT-cellulose, etc., may be used.

The mRNA can be also prepared using a kit, such as Fast Track mRNA Isolation Kit (manufactured by Invitrogen), Quick Prep mRNA Purification Kit (manufactured by Pharmacia), or the like.

To synthesize cDNA from RNA extracted from an ovary or placenta of animals such as a bovine or a human wherein VSGF is expressed, a method is employed to synthesize cDNA with the mRNA using a reverse transcriptase as a template, according to Okayama-Berg method [Mol. Cell Biol., 2, 161 (1982)], Gubler and Hoffman method [Gene, 25, 263 (1983)], etc. Alternatively, method using a commercially available kit, such as SUPERSCRIPT Plasmid System for cDNA Synthesis and Plasmid Cloning (manufactured by Life Technologies) or ZAP-cDNA Synthesis Kit (manufactured by Stratagene) is employed to synthesise cDNA.

To insert cDNA into a vector, a method is employed comprising inserting cDNA into a plasmid vector or a phage vector according to the methods of Sambrook et al. [EMBO J., 4, 91 (1985)] and Hyunh, T. V. et al. [A practical Approach, edited by D. M. Glover, vol. 1, 49, IRL Press, Oxford]. In these methods, cDNA may be synthesized in a mRNA annealed with a plasmid vector or a phage vector to which a dT tail has been added, and the synthesized cDNA is inserted into a plasmid vector or a phage vector.

The plasmid vector or phage vector used for inserting cDNA can be those which can autonomously replicate in a host cell and stably keep the cDNA. Examples are plasmids such as pBR322 and pUC119, a phage vector such as λgt10 [DNA Cloning, A Practical Approach, 1, 49 (1985)].

In the instance where a cDNA is inserted into a plasmid vector, a cDNA library is constructed by transforming a host cell by introducing the plasmid vector to an appropriate host cell such as *Escherichia coli* and *Bacillus bacterium* by the electroporation or calcium chloride method. In the case where the cDNA is inserted into a phage vector, a cDNA library is constructed by transducing the phage vector into proliferated host cell by in vitro packaging method.

Transformants comprising cDNA that encodes VSGF can be selected from the constructed cDNA library as follows.

The transformants can be obtained by determining the nucleotide sequences of the cDNAs of the transformants, comparing the amino acid sequences encoded by the nucleotide sequence with amino acid sequences of a peptide fragment obtained from the purified VSGF protein by a conventional method, and by selecting a transformant comprising cDNA encoding an amino acid sequence highly homologous to that of the purified VSGF protein.

Alternatively, the transformants can be obtained by carrying out plaque hybridization or colony hybridization using a labeled DNA probe prepared based on an amino acid sequence data of the bovine VSGF that was determined from a VSGF protein, and by selecting a transformant which is hybridizable. As a DNA probe used for hybridization, any of chemically synthesized genomic DNA, cDNA and a DNA may be used, so long as it encodes VSGF.

Once, the DNA encoding VSGF is obtained and a nucleotide sequence thereof is determined in the above-descrived manner, the DNA of interest can be amplified by PCR [PCR Protocols, Academic Press(1990)] by preparing primers based on the nucleotide sequence and using cDNA synthesized from the mRNA or a cDNA library as the templete.

A plasmid or a phage comprising cDNA encoding VSGF of the present invention includes plasmid pcDNA3HVSGF. *Escherichia coli* HVSGF, which is an *Escherichia coli* comprising pcDNA3HVSGF, was deposited with the National Institute of Bioscience and Human-Technology, Agency of Industrial Science and Technology, Japan, on Jun. 12, 1997 with accession number FERM BP-5965 under the Budapest Treaty.

The nucleotide sequence of cDNA encoding the obtained VSGF can be determined by Maxam and Gilbert method and dideoxyribonucleotide sequencing [Proc. Natl. Acad. Sci. U.S.A., 74, 5463 (1977)], etc.

A transformant expressing the VSGF of the present invention can be obtained by introducing into a host cell a recombinant vector, which is prepared by inserting a DNA (VSGF-DNA, hereinafter) encoding the VSGF obtained by methods mentioned above, into the downstream of the promoter of an appropriate vector. Specifically, a DNA fragment comprising a VSGF-DNA is fragmented with an appropriate length comprising the VSGF-DNA by restriction enzyme or DNAase and the fragments are inserted into the downstream of the promoter of the expression vector. The expression vector into which the DNA fragments are inserted is introduced into a host cell suitable for the expression vector.

As a host cell, any cells such as microorganism, yeast, animal cells, and insect cells capable of expressing the gene can be used. Microorganisms used as a host are microorganisms of genera such as Escherichia, Serratia, Corynebacterium, Brevibacterium, Pseudomonas, and Bacillus including species such as *Escherichia coli, Bacillus subtilis, Bacillus amyloliquefaciens, Brevibacterium flavum, Brevibacterium lactofermentum, Corynebacterium glutamicum,* and *Microbacterium ammoniaphilum*. Specific examples of such microorganism are *Escherichia coli* XL1-Blue, *Escherichia coli* XL2-Blue, *Escherichia coli* JM109, *Escherichia coli* DH1, *Escherichia coli* MC1000, *Bacillus subtilis* ATCC6051, *Bacillus amyloliquefaciens* ATCC23842, *Brevibacterium immariophillum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium acetoacidophilum* ATCC13870, and *Microbacterium ammoniaphilum* ATCC15354.

Yeasts used as a host include *Saccharomyces cerevisiae, Schizosaccharomyces pombe, Kluyveromyces lactis, Trichosporon pullulans, Schwanniomyces alluvius*. Specific examples of such yeast are *Saccharomyces cerevisiae* ATCC56072, *Schizosaccharomyces pombe* ATCC2476, *Kluyveromyces lactis* ATCC8563, *Trichosporon pullulans* ATCC10677, and *Schwanniomyces alluvius* ATCC26074.

Animal cells used as a host include namalwa cell derived from human, COS cell derived from monkey, and Chinese Hamster Ovary (CHO) cell derived from Chinese hamster.

Insect cells used as a host include Sf9 and Sf21 derived from oocyte of Spodoptera frugiperda [Baculovirus Expression Vectors, a Laboratory Manual 1992 edition, by Oreilly, Miller, Luckow, published by W. H. Freeman & Company, New York (hereinafter, Baculovirus Expression Vectors: a Laboratory Manual)] and Tn5 derived from the egg of Trichoplusia ni and commercially available from Pharmingen Co. as a commercial name, High5.

Expression vectors used are those which are capable of autonomously replicating in the host cells mentioned above and of combining with a chromosome, and contain a promoter located in the site capable of transcribing the VSGF-DNA.

When a microorganism such as *E. coli* is used as a host cell, it is preferable that the expression vector comprise a promoter, a ribosome binding sequence, the VSGF-DNA of the present invention, a termination sequence, and in some cases the controlling region of a promoter, as well as being capable of autonomously replicating in a microorganism.

The expression vectors include pTZ18RP1 (Japanese Published Unexamined Patent Application No. 117292/92), pMALTM-c2 (New England Bio Labos Co.), pBTrp2, pBTac1, and pBTac2 (commercially available from Boehringer Ingelheim Corp.), pBluescript (Stratagene Co.).

The expression vector may comprise genes controlling a promoter. Any promoter capable of being expressed in a host cell such as *Escherichia coli* can be used. Examples of such promoter are trp promoter, lac promoter, PL promoter, and PR promoter, that are all derived from *E. coli* bacterium and phages. In addition, a promoter, which is artificially modified, such as tac promoter, can be used.

As a ribosome binding sequence, any sequences which are capable of being expressed in a host cell such as *Escherichia coli* may be used. Preferably, a plasmid wherein a distance between the ribosome binding site and a start codon is adjusted to a proper distance such as 6–18 bases is used. A termination sequence is not necessarily required for expression of the gene, however, it is preferable that the gene is located immediately beneath a structural gene.

A vector is introduced into a bacterium by any method to introduce a DNA into a bacterium; for example, the method comprising using calcium ions [Proc. Natl. Acad. Sci. USA, 69, 2110–2114 (1972)] and the method comprising using protoplast (Japanese Published Unexamined Patent Application No. 2483942/88).

In case of using a yeast strain as a host cell, the expression vector includes YEp13 (ATCC37115), YEp24 (ATCC37052), and YCp50 (ATCC37419).

Any promoters capable of being expressed in a host cell of the yeast strain can be used. Examples of such promoter include a promoter of gene of the glycolysis system such as hexokinase, gal 1 promoter, gal 10 promoter, a promoter of heat shock protein, MF α 1 promoter, and CUP 1 promoter.

To introduce a recombinant vector into a yeast, any methods to introduce a DNA into a yeast may be used, including the electroporation method [Methods in Enzymol., 194, 182 (1990)], the sphaeroplast method [Proc. Natl. Acad. Sci., USA, 84, 1929 (1978)], and lithium acetate method [J. Bacteriology, 153, 163 (1983)].

In case of using an animal cell as a host cell, pcDNA I/Amp, pcDNA I, pcDM8 (commercially available from Funakoshi Co.) and pKA1 (Japanese Published Unexamined Patent Application No. 117292/92) can be used.

As the promoter, any promoters capable of being expressed in a host cell derived from animals can be used. For example, a promoter of IE (immediate early) gene of human CMV can be used. In addition, the enhancer of the IE gene of the human CMV can be used together with the promoter.

To introduce a recombinant vector into an animal cell, any methods for introducing a DNA into an animal cell can be used, including electroporation method [Cytotechnology, 3, 133 (1990)], calcium phosphate method (Japanese Published Unexamined Patent Application No. 227075/90), and lipofection method [Proc. Natl. Acad. Sci., USA, 84, 7413 (1987)].

In case that an insect cell is used as a host cell, insect cells expressing a protein are obtained by introducing a vector for introducing a recombinant gene and a baculovirus into an insect cell, obtaining a recombinant virus in supernatant of the culture of the insect cell, and infecting the recombinant virus to the insect cell.

Vectors for introducing gene include pVL1392, pVL1393, and pBlueBacIII (Invitrogen Co.).

Baculovirus includes Autographa californica nuclear polyhedrosis virus, which is a virus infecting insects belonging to Barathra.

A method for co-introduction of the above baculovirus and the above vector for introducing the recombinant gene into an insect cell to prepare a recombinant virus includes calcium phosphate method (Japanese Published Unexamined Patent Application No. 227075/90) and lipofection method [Proc. Nat i. Acad. Sci., USA, 84, 7413 (1987)].

The transformant obtained by the method mentioned above is cultivated by a method conventionally used for polypeptide production using transformant.

As a medium, any of natural or synthetic culture medium may be used, so long as it contains carbon source, nitrogen source, and inorganic salts which can be assimilated by microorganisms used and transformant is cultivated efficiently.

As a carbon souce, any carbon source which can be assimilated by a used microorganism may be used, including glucose, fructose, sucrose, molasses containing them, carbohydrates such as starch and hydrolysate of starch, organic acids such as acetic acid and propionic acid, and alcohols such as ethanol and propanol.

Nitrogen sources used include ammonia, ammonium salts of various inorganic and organic acids such as ammonium chloride, ammonium sulfate, ammonium acetate, and ammonium phosphate, other nitrogen-containing compounds, peptone, meat extracts, yeast extracts, corn steep liquor, casein hydrolysates, soybean cakes, hydrolysate of soybean cake, and various fermenting bacterial cells and digests thereof.

Inorganic substances used are potassium phosphates, magnesium phosphate, magnesium sulfate, sodium chloride, ferrous sulfate, manganese sulfate, copper sulfate, and calcium carbonate.

Cultivation is carried out under aerobic conditions such as shaking culture or deep aerating agitation culture at 15–40° C. for 16–96 hours at pH of 3.0–9.0. The pH is adjusted by adding inorganic or organic acids, alkali solution, urea, calcium carbonate, ammonia, etc.

During cultivation, antibiotics such as ampicillin and tetracycline can be added to the medium, if necessary.

In the case of cultivating microorganisms transformed by an expression vector using an inductive promoter, an inducer can be added to the culture medium, if necessary. For example, isopropyl-β-D-galactopyranoside (IPTG) can be added to the culture medium for cultivation of microorganisms transformed by an expression vector using lac promoter; and indole acrylate (IAA) can be added to the culture medium for cultivation of microorganisms transformed by an expression vector using trp promoter.

As a medium for cultivating a transformant obtained by using an animal cell as a host cell, RPMI1640 medium [The Journal of the American Medical Association 199, 519 (1967)], Eagle's MEM medium [Science, 122, 501(1952)], or media obtained by adding bovine infantile serum to the above media.

As a medium for cultivating a transformant obtained by using an insect cell as a host cell, TNM-FH medium (manufactured by Pharmingen Co.), Sf9001 ISFM (Life Technologies Co.), ExCell400 and ExCell405 (both are manufactured by JRH BioSciences Co.) can be used.

Cultivation is carried out in the presence of 5% $CO_2$ at 35–37° C. for 3 to 7 days.

Antibiotics such as Kanamycin and Penicillin can be added to culture medium, if necessary.

Thus, VSGF-DNA of the present invention can be directly expressed. With regard to the gene expression method, a secretion production, a fusion protein expression and the like can be effected in accordance with the method described in Molecular Cloning, $2^{nd}$ ed, in addition to the direct expression.

Examples of the fusion proteins are a maltose-binding protein/P100 fusion protein produced by the transformant which is obtained by transforming Escherichia coli JM109 using plasmid pMALP100 prepared by inserting VSGF-DNA between XmnI and SalI sites of plasmid pMALTM-c2 (New England Bio Labos Co.).

When VSGF-DNA is expressed as a fusion protein, the VSGF site can be isolated by cleavage with a suitable protease. Such protease includes factor Xa (New England Bio Labos Co.).

The target protein can be isolated and purified from a culture by a combination of a known separation process, such as treatment with denaturant such as urea or with a detergent, ultrasonic treatment, enzymatic digestion, salting-out and solvent precipitation, dialysis, centrifugation, ultrafiltration, gel filtration, SDS-PAGE, isoelectric focusing, ion exchange chromatography, hydrophobic chromatography, affinity chromatography, and reversed phase chromatography.

An antibody can be prepared by immunizing an animal by using as an antigen a peptide of the present invention or by using a peptide that is a portion of protein of the present invention which is chemically synthesized on the basis of the amino acid sequence represented by SEQ ID NO: 1, 3 or 5 as an antigen.

A monoclonal antibody can be obtained by: preparing an antigen and immunizing an animal with the antigen, fusing an immunized animal cell and a myeloma cell to give a hybridoma; and cultivating the hybridoma and collecting the culture medium or administering the hybridoma to an animal to cause ascites tumors and collecting the ascites. A polyclonal antibody can be prepared by collecting serum of an immunized animal.

The immunization of an animal is carried out as follows. An antigen prepared as described below is administered subcutaneously, intravenously, or abdominally to non-human mammal such as mouse, rat, and hamster of 3–20 week old, and collecting antibody-forming cells in spleen cells, lymph nodes, or in peripheral blood of the animal.

The antigen is prepared by separating and purifying VSGF from an organ or cell line of various animals, including humans. Alternatively, the antigen is prepared by introducing, into a host cell such as $E.$ $coli,$ yeast, animal cells, or insect cells, a recombinant vector comprising DNA which encodes a protein having an amino acid sequence represented by SEQ ID NO: 1, 3 or 5 or having an amino acid sequence wherein one or more amino acid residues are substituted, deleted, or added in the amino acid sequence represented by SEQ ID NO: 1, 3, or 5, or encodes a polypeptide having a portion of the amino acid sequence, into a host cell such as *E. coli,* yeast, animal cells, or insect cells to express a protein or a polypeptide. A polypeptide having a partial sequence can be obtained by synthesizing with an amino acid synthesizer. For immuization, the antigen obtained can be administered after binding with a carrier protein (e.g., Keyhole Limpet hemocyanin and bovine serum albumin) having a high immunogenicity by chemical modification or can be administered together with an appropriate adjuvant (e.g., Complete Freund's Adjuvant, aluminium hydroxide gel, and pertussis vaccine).

The antigen is administered to an animal at 1–2 week intervals after the first administration 5–10 times in total. Blood is collected from a venous plexus on eyegrounds on 3rd–7th days after each administration, and reactivity of the serum to an antigen is examined by enzyme imunoassay (Antibodies—a Laboratory Manual, Published by Cold Spring Harbor Laboratory in 1988; details are given later.), etc. The non-human animal, the serum of which showed enough antibody titer against the antigen used for immunization, is provided as a source of antigen-forming cells. A polyclonal antibody is obtained by separating and purifying serum obtained from the animal.

As myeloma cells, a cell line obtained from a mouse can be used. For example, used are 8-azaguanine resistant mouse (BALB/c derived)-myeloma cell line P3-X63Ag8-U1 (P3-U1) [Current Topics in Microbiology and Immunology, 18, 1–7, (1978)], P3-NS1/1-Ag41(NS-1) [European J. Immunology, 6, 511–519, (1976)], SP2/O-Ag14(SP-2) [Nature, 276, 269–270 (1978)], P3-X63-Ag8653(653) [J. Immunology, 123, 1548–1550, (1979)], P3-X63-Ag8(X63) [Nature, 256, 495–497, (1975)].

The antibody-forming cells and myeloma cells obtained above are mixed, suspended in HAT culture medium (which is obtained by adding hypoxanthine, thymidine, and aminopterin to a normal culture medium), and cultivated for 7 to 14 days. After cultivation, a part of the supernatant of the culture medium is examined by enzyme immunoassay, etc. to select cells that are reactive to the VSGF used as an antigen and not reactive to a protein not containing the VSGF. Furthermore, cloning is carried out by the limiting dilution method and a cell line stably having a high antibody titer by enzyme immunoassay is selected as an anti-VSGF monoclonal antibody-forming hybridoma.

A monoclonal antibody can be prepared by cultivating the hybridoma cells and collecting and purifying the culture medium, or by administering hybridoma cells into an abdominal cavity of an animal to form ascites therein and collecting and purifying the ascites.

A polyclonal antibody and monoclonal antibody are purified by a method such as centrifugation, precipitation with ammonium sulfate, precipitation with caprylic acid, or a combination of some of chromatography by using DEAE-Sepharose column, anion exchange column, protein A or protein G column, or gel filtration column.

Selection of an Anti-VSGF Monoclonal Antibody (Enzyme Immunoassay)

A recombinant VSGF or purified VSGF is used as an antigen, and is poured in a 96-well plate at a concentration of 1–50 μg/ml in an amount of 10–100 μl/well, kept at 4° C. overnight, and coated over the plate. After blocking the antigen with BSA solution, the cultured media of the hybridoma or purified antibody obtained as the first antibody by the method mentioned above is poured in an amount of 50–100 μl/well, and reaction is carried out at room temperature for 2 hours or 4° C. overnight. After washing with a solution of PBS or a solution in which 0.05% Tween-20 has been added to PBS (Tween-PBS), 1–50 μg/ml of anti-mouse immunoglobulin antibody or anti-rat immunoglobulin antibody, that has been labeled with biotin, enzyme, chemiluminescent substance, or radioactive compound, as the second antibody is poured in an amount of 50–100 μl/well, and reaction is carried out at room temperature for 1–2 hours. After washing well, reaction is carried out according to the labelling substance of the second antibody to select wells specifically reacting to the VSGF as anti-VSGF monoclonal antibody.

The antibody thus obtained is effective for immunological detection of a diagnosis of wound healing failure, intractable skin ulcer, or a tissue or a cell of abnormal blood vessel formation disease by, for example, fibroblast growth factor.

The method for detecting a disease in which the morbid states progress by abnormal blood vessel formation includes a fluorescent antibody method, an enzyme-linked immunosorbent assay (ELISA), a radioactive material labeled immunoassay (RIA), an immunocyte staining method, an immunotissue staining method, Western blotting method, an immunoprecipitation method, and the like.

The fluorescent antibody method comprises the steps of: (a) separating human cell or a crushing solution thereof, tissue or a crushing solution thereof, serum, preural fluid, ascites fluid, ocular fluid or the like to prepare a sample; (b) reacting the separated sample prepared in the step (a) with the monoclonal antibody of the present invention; (c) further reacting the reacted sample prepared in the step (b) with an anti-mouse IgG antibody or binding fragment labeled with a fluorescence substance, such as fluorescin isothiocyanate (FITC) or the like; and (d) measuring the fluorescence substance with a flow cytometer.

The enzyme-linked immunosorbent assay (ELISA) comprises the steps of: (a) separating human cell or a crushing solution thereof, tissue or a crushing solution thereof, serum, preural fluid, ascites fluid, ocular fluid or the like to prepare a sample; (b) reacting the separated sample prepared in the step (a) with the monoclonal antibody of the present invention; (c) further reacting the reacted sample prepared in the step (b) with an anti-mouse IgG antibody or binding fragment labeled with an enzyme, such as peroxydase, biotin or the like; and (d) measuring the resultant developed dye with an absorption measuring apparatus.

The radioactive material labeled immunoassay (RIA) comprises the steps of: (a) separating human cell or a crushing solution thereof, tissue or a crushing solution thereof, serum, preural fluid, ascites fluid, ocular fluid, or the like to prepare a sample; (b) reacting the separated sample prepared in the step (a) with the monoclonal antibody of the present invention; (c) further reacting the reacted sample prepared in the step (b) with an anti-mouse IgG antibody or binding fragment labeled with radioactive ray; and (d) measuring the radioactive ray with a scintillation counter or the like.

The immunocyte staining and immunotissue staining methods comprise the steps of: (a) separating human cell, tissue or the like to prepare a sample; (b) reacting the separated sample prepared in the step (a) with the monoclonal antibody of the present invention; (c) further reacting the reacted sample prepared in the step (b) with an anti-mouse IgG antibody or binding fragment labeled with a fluorescence substance, such as fluorescin isothiocyanate (FITC), or the like, or an enzyme, such as peroxydase, biotin, or the like; and (d) observing the cell, tissue or the like with a microscope.

Examples of the methods, using the monoclonal antibody of the present invention, for immunologically detecting VSGF or a cell in which VEGF is expressed on the surface thereof and for immunologically detecting and determining soluble VSGF include immunocyte staining, Western blotting, sandwich ELISA, and the like.

The present invention is described in detail with referring to Examples.

Basic operation and enzyme reaction for DNA recombination were carried out according to well-known methods (Molecular Cloning: a Laboratory Manual. Cold Spring Harbor Laboratory, 1989). Restriction enzymes and various modification enzymes used were those manufactured by Takara Shuzo Co., unless described otherwise. The composition of buffer solution and the condition of reactions for various enzymes were followed.

In the present invention, amino acids and peptides are indicated according to the abbreviation that was adopted by IUPAC-IUB-Biochemical Nomenclature Committee. In case that any optical isomers can exist for amino acid, the optical isomers are regarded as L-types, unless indicated otherwise.

The left terminal of deoxyribonucleotide sequence indicates 5' terminal, unless mentioned otherwise.

The present invention is described in detail with referring to Examples.

EXAMPLES

Example 1

Purification of Bovine VSGF

About 1000 bovine ovaries kept at −70° C. by freezing immediately after collection at a slaughter-house, were melted at 4° C. and the fluid portion was collected by suction. The obtained fluid was centrifuged at 5000 rpm for 20 minutes and the supernatant was used as bovine follicular fluid (bFF).

To 1 liter of bFF was added 4 liter of buffer solution A {10 mM tris-HCl, 0.1% 3-[(3-cholamide propyl) dimethylammonio]-1-propane sulfonate (CHAPS), 1 mM EDTA, 10 mg/l leupeptin, 10 mg/l phenylmethylsulfonylfluoride (PMSF); pH 7.5}, and sodium chloride (NaCl) was also added to make the final concentration to 0.4 M. Heparin-Sepharose column (Pharmacia Biotech Co.) of 5.0× 2.0 cm was equilibrated with buffer solution A containing 0.35 M NaCl, and the target protein was adsorbed by passing the bFF solution through a column. 200 ml of buffer solution A containing 0.35 M NaCl was passed through the column to wash the column. Then, 200 ml of buffer solution A containing 0.75 M NaCl was passed through the column to elute the target protein. The amount of protein contained in the eluate was 70 mg.

The above eluate (200 ml; protein amount:70 mg) was diluted by adding 1.4 L of buffer solution A to make NaCl concentration to 0.1 M. DEAE-Fractogel 650 column (Mitsubishi Kagaku Co.) of 1.0×2.0 cm was equilibrated with buffer solution A containing 0.1 M NaCl, and the diluted eluate was passed through the column to adsorb the target protein. 10 ml of buffer solution A containing 0.1 M NaCl was passed through the column to wash and 10 ml of buffer solution A containing 0.5 M NaCl was passed through the column to elute the target protein. The amount of protein contained in the eluate was 32.1 mg.

Figure 2:
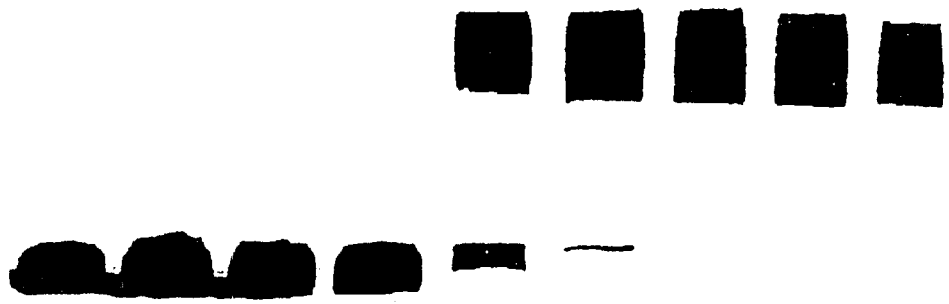
FIG. 2 shows the result of SDS-PAGE of a part of each fraction of FIG. 1.

The eluate (10 ml; protein amount: 32.1 mg) was diluted by adding buffer solution A (40 ml) to make NaCl concentration 0.1 M. A DEAE Sepharose CL4B (Pharmacia Biotech Co.) column of 1.0×7.0 cm was equilibrated with buffer solution A containing 0.1 M NaCl and the diluted eluate was passed through the column to adsorb the target protein. 30 ml of buffer solution A containing 0.1 M NaCl was passed through the column to wash the column and buffer solution A (200 ml) was subjected to a linear concentration gradation of NaCl (0.1 M–0.5 M) to elute the target protein. The flow rate was 45 ml/h, and eluate was fractioned by 3 ml (67 fractions in total). FIG. 1 shows absorbance of each fraction at 280 nm and the vascular smooth muscle cell growth promotion activity. FIG. 2 shows the result of non-reductive sodium dodecyl sulfate-polyacrylamide gel electrophoresis (SDS-PAGE) carried out by using 4–20% gradient gels (MultiGel 4–20 manufactured by Daiichi Pure Chemicals Co.) for eluted fraction numbers 22–25 and fraction Nos. 28–32 that showed higher values at A280 nm in FIG. 1.

The vascular smooth muscle cell growth promotion activity was measured by the following methods.

Measurement of vascular smooth muscle cell growth promotion activity

Bovine aortic smooth muscle cells (BASMC) isolated and cultivated according to explant method [(J. Cell Biol., 50, 172 (1971)] was inoculated on Dalbecco's modified Eagle medium (DMEM), (Gibco BRL Co.) containing 10% fetal calf serum (FCS) in 10-cm petri dish in an amount of $5 \times 10^5$/dish, and make a passage for every three days to use passages up to 12.

BASMC dissolved in DMEM containing 2% FCS was poured into a 24-well plate in an amount of $5 \times 10^3$/well, incubated overnight, and cells adhered to the plate. Then, a test sample dissolved in 0.5 ml DMEM containing 2% FCS was added thereto, and incubated for three days. After the incubation, 0.25% trypsin and 0.2% ethylenediamine tetracetic acid (EDTA) were added thereto, and cells were suspended therein to count their numbers with a cell counter (Coulter Counter manufactuered by Coulter Co.) The growth promotion activity is calculated based on the following formula.

Growth promotion activity (%)=(A/B)×100

A: cell number after cultivation with DMEM containing 2% FCS with test samples.

B: cell number after cultivation with DMEM containing 2% FCS without test samples.

Figure 3:
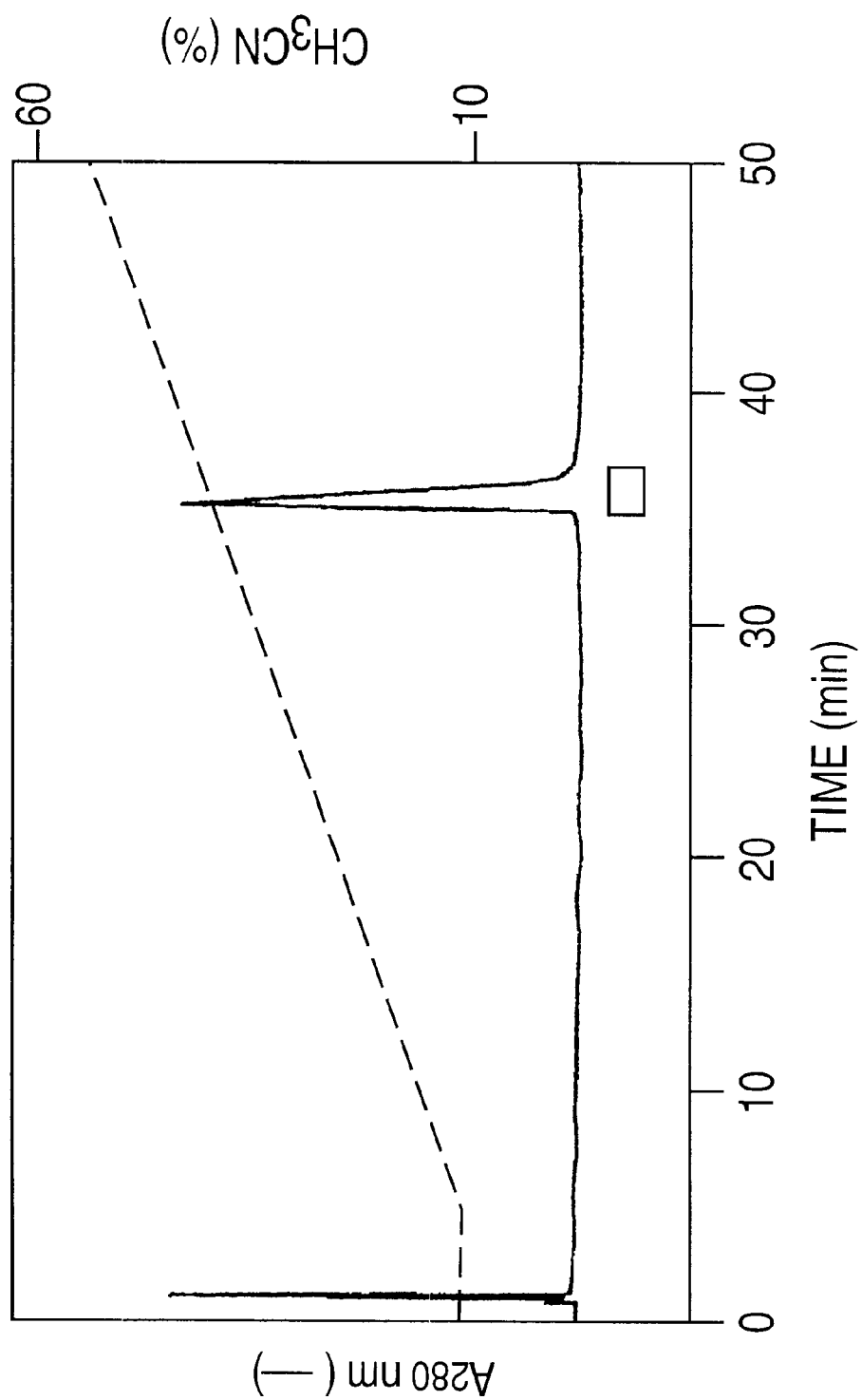
FIG. 3 shows elution pattern at purification of a bovine VSGF by reversed phase HPLC. The bold line beneath the peak in the graph shows the range of fractionation.
Figure 4:
FIG. 4 shows the result of SDS-PAGE of bovine VSGF finally purified.

According to the result obtained by the above measurement, the fractions of Nos. 28–32 were collected (15 ml; protein content: 6.8 mg) and 1 ml of the collection was purified by high Performance Liquid Chromatography (HPLC) using a reversed phase column (4.6×50 mm: Nakalai Tesque). Elution was carried out with a linear concentration gradient of 10–60% acetonitrile in 0.1% TFA aqueous solution (0–5 min; 10% acetonitrile, 5–55 min; 10–60% acetonitrile concentration gradient, 55–70 min.; 60% acetonitrile, flow rate; 1 ml/min.). FIG. 3 shows the elution pattern detected with absorbance at 280 nm. A peak portion detected was fractioned and collected to confirm purity by non-reductive SDS-PAGE. The result is shown in FIG. 4. From the result, it was confirmed that the VSGF was purified as a single substance and the molecular weight of the VSGF was in the range between 88 and 95 kDa.

Further, 14 ml of remained collection was purified by the reversed phase HPLC method and 3.2 mg of protein was obtained. As described above, the protein showed vascular smooth muscle cell growth promotion activity, and therefore, the protein is named as vascular smooth muscle cell growth factor (VSGF).

Example 2
Determination of Partial Amino Acid Sequence of Bovine VSGF

The bovine VSGF (1 mg) purified in Example 1 was subjected to a reductive carboxymethylation according to a conventional method, and digested with lysylendopeptidase (Sigma Co.) overnight to collect the digest by HPLC with a reversed phase column (C18 Cosmosil, Nakalai Tesque). Among peaks composed of peptides obtained by digestion, the amino acid sequence of 17 peptides were partially determined using a protein sequencer (Applied Biosystems Co.; Model 492). The sequence was shown in SEQ ID Nos.: 9–21.

Example 3
Cloning of cDNA of Bovine VSGF

Bovine ovaries preserved after being frozen at −70° C. with liquid nitrogen immediately after collection was used to prepare an RNA by Acid GTC method [Anal. Biochem., 162, 156–159 (1987)] (yield of a total RNA obtained from 3 g of ovaries: 8.96 mg). Furthermore, mRNA (25 μg) was prepared with an Oligotex Super (Daiichi Pure Chemicals Co.) Ten μg of this mRNA was used for synthesizing cDNA by using an Oligo-dT-priming (Pharmacia Co.). The cDNA was bound to EcoRI-NotI Adapter (Pharmacia Co.) and ligated to λgt10 phage (Stratagene Co.) and subjected to Gigapack Gold II (InvitroGen Co.) in vitro packaging to obtain non-amplified cDNA library containing $3.1 \times 10^6$ independent clones.

Sequences suitable for cDNA cloning were selected from the partial amino acid sequences previously determined, and DNAs having the sequences represented by SEQ ID Nos.: 7 and 8 were synthesized. For 200 ng of each sequence, the 5' terminal was labeled with γ-32 P-ATP (Amersham Co.). The radioactivity of each sequence was 60,000,000 cpm/400 μl (300 cpm/pg). The probe thus prepared was used for screening of 5000 clone/petri dish through the following steps.
(1) Pre-hybridization: 6×SSC (Wako Pure Chemicals Co.) 5×Denharts (Wako Pure Chemicals), 0.1 mg/ml salmon sperm DNA (Sigma Co.), 37° C., 4 hours.
(2) Hybridization: 6×SSC, 5×Denharts, 0.1 mg/ml salmon sperm DNA, labeled probe 50 μl (1000 cpm, 32 ng), 37° C., 24 hours.
(3) Washing:
  1) 6×SSC, 0.1% sodium dodecyl sulfate, 42° C., 20 min.×2.
  2) 3 M tetramethylammonium chloride, 50° C., 20 min.×2.
(4) Exposure to light: −70° C., 24 hours.

As a result, two positive clones were obtained and these clones were named VSGF-1 and VSGF-2, respectively. VSGF-1 was about 4.2 kb and VSGF-2 was about 3.5 kb; a non-translated region of the 3' terminal side of VSGF-1 was short.

The two clones were subcloned with Bluescript KS (Stratagene Co.) and a restriction enzyme map was constructed. The clones were furthermore subcloned and finally their nucleotide sequences were determined by dideoxyribonucleotide sequencing method [Proc. Natl. Acad. Sci. U.S.A., 74, 5463 (1977)]. The determined nucleotide sequence and amino acid sequences of translated proteins are shown in SEQ ID Nos. 4 and 3, respectively. From the result, it was found that the bovine VSGF is a protein comprising 807 amino acid residues and the protein is a secretory protein having a signal sequence comprising 28 amino acid residues at the N-terminal on the basis of sequence analysis and there exists three N-glycosylation sites in the amino acid sequence. (214th to 216th residues, 447th to 449th residues, and 681st to 683rd residues).

Example 4
Gene Cloning of Human VSGF

A cDNA of human VSGF was cloned based on cDNA library of a human ovary using a bovine VSGF as a probe as follows.

An insert of a bovine VSGF with the entire sequence was randomly labeled with 32P-dDCTP (Amersham Co.), and it was used as a probe. A cDNA library was prepared from a human ovary by using oligo-dT-primer (Pharmacia Co.), and it was introduced into λgt10 phage vector to obtain $1 \times 10^6$ independent clones. Two positive clones were obtained using the above probe by the similar method for the bovine VSGF cloning. One of them had a total length of 3.1 kb and its nucleotide sequence was determined by the similar method to that of the bovine VSGF. The, nucleotide sequence is shown in SEQ ID NO: 2 and the amino acid sequence of the translated protein is shown in SEQ ID NO: 1.

Example 5
Expression of Human VSGF Protein

Figure 5:
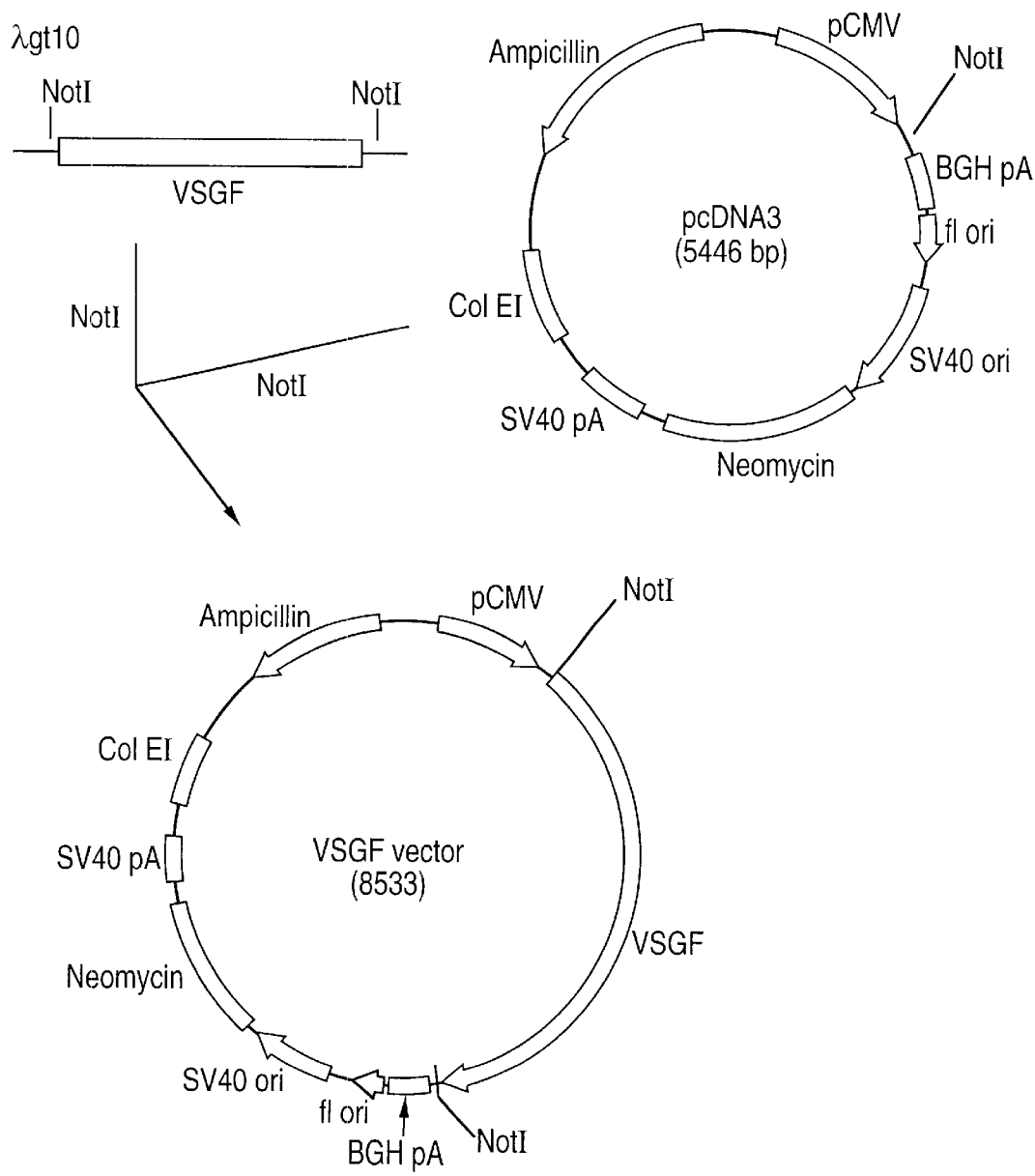
FIG. 5 shows the structure of expression vector for recombinant human VSGF.

A human cDNA insert was isolated by NotI digestion and introduced at NotI site of pcDNA3 (mammalian expression vector, manufactured by Invitrogen Co.) in ordinary direction. FIG. 5 shows the structure of a recombinant vector. *Escherichia coli* HVSGF, which is an *Escherichia coli* comprising pcDNA3HVSGF, was deposited with the National Institute of Bioscience and Human-Technology, Agency of Industrial Science and Technology, Japan, on Jun. 12, 1997 with accession number FERM BP-5965 under the Budapest Treaty. The human VSGF pcDNA3 plasmid was transfected to COS-7 cells by lipofection method and a permanent cell line was established by using DMEM containing 10% FCS in which G418 was adjusted to a final concentration of 200 μg/ml. The secretion of human VSGF from G418 resistant COS-7 cells was confirmed by using the enzyme-linked immunosolvent assay (ELISA) method. The method is described below.

ELISA Method

VSGF(5 μg/ml) was coated on a 96-well plate, PBS containing 0.4% Block Ace that is prepared by diluting an anti-bovine VSGF antibody by 30000 times was added thereto, and it was left at room temperature for 2 hours. Then, a blocking solution (1% Block Ace) was added, and it was left at room temperature for 1 hour. After washing, alkaliphosphatase-labeled anti-rabbit immunoglobulin antibody (EY Laboratories Co., 1000 times dilution) was added, and it was left at 4° C. for 24 hours. After coloration by a reaction with PNPP (Scimed Life Systems, Inc.) at room temperature for 2 hours, measurement was carried out at 410 nm.

Figure 6:
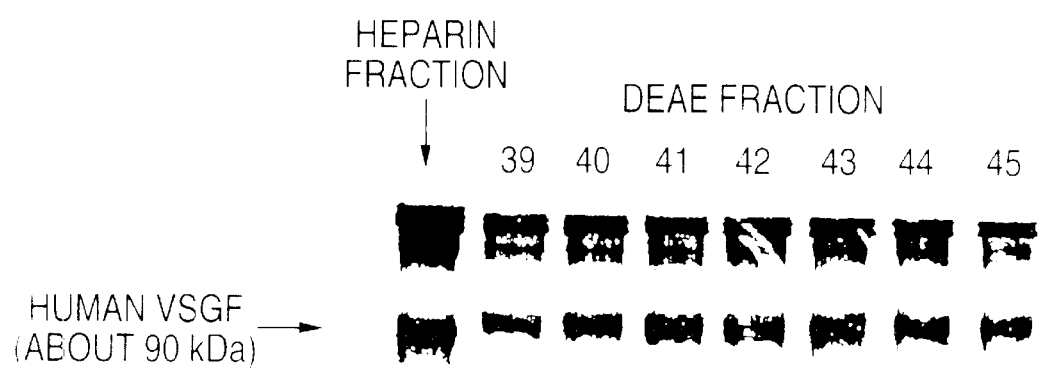
FIG. 6 shows the result of SDS-PAGE of recombinant human VSGF expressed in a COS-7 cell.

After the confirmation of secretion of the human VSGF by the above method, a culture medium obtained from cultivation of G418 resistant COS-7 cell was centrifuged to recover the supernatant. The human VSGF was purified from the supernatant as in Example 1 as described below. Heparin-Sepharose column was equilibrated with buffer solution A containing 0.35 M NaCl, and the supernatant was passed through the column to adsorb the target protein. Heparin—Sepharose column was washed with buffer solution A containing 0.35 M NaCl, and the target protein was eluted with buffer solution A containing 0.75 M NaCl. Then, DEAE-Sepharose CL4B column was equilibrated with buffer solution A containing 0.1 M NaCl, and the eluate obtained above was passed through the column to adsorb the target protein. Next, buffer solution A was subjected to a linear concentration gradient of NaCl (0.1–0.5M) to elute human VSGF, which is the target protein. For fraction Nos 39–45 of eluate showing higher absorbance at 280 nm, the result of non-reductive SDS-PAGE by using a 10% gel is shown in FIG. 6.

Figure 7:
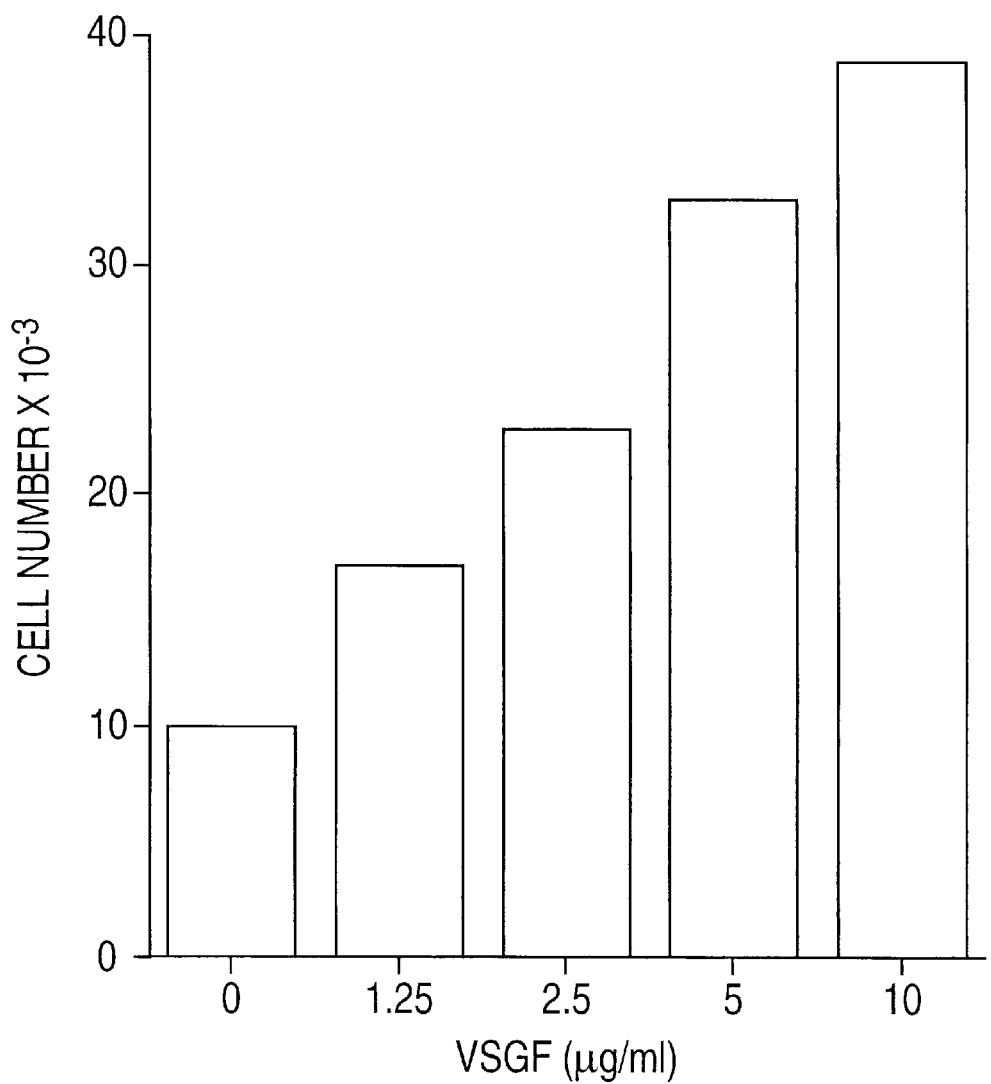
FIG. 7 shows increase in measured cell number that corresponds to smooth muscle cell growth-inhibiting activity of a human recombinant VSGF.

Example 6
Vascular Smooth Muscle Cell Growth Promotion Activity of Recombinant Human VSGF The vascular smooth muscle cell growth promotion activity of recombinant human VSGF produced in Example 5 was measured by the method described in Example 1. The result is shown in FIG. 7.

Example 7
Preparation of Anti-bovine VSGF Polyclonal Antibody

Bovine VSGF (0.5 mg) was administered together with a complete adjuvant to three rabbits (Body weights are 2.0 kg, 2.1 kg, and 2.15 kg each, Japanese White) to prepare an antibody against the bovine VSGF. The body weights of the rabbits at the final immunization were 3.0 kg, 3.4 kg, and 3.6 kg. Serum antibody titer was tested by the ELISA method described in Example 5. In addition, the cross reactivity of this antibody against the human VSGF was tested by the ELISA method and it was found that the antibody reacts to the human VSGF and its affinity was almost equal to both the human and bovine VSGFs.

Example 8
Preparation of Anti-human VSGF Monoclonal Antibody (1) Immunization of animals and preparation of antibody-forming cells The human VSGF (30 $\mu$g) prepared in Example 5 was administered to a five-week old rat (SD) and a mouse (Bal b/c) together with 2 mg of aluminium gel and $1 \times 10^9$ cells of pertussis vaccine (Chiba-ken Kessei Kenkyusho), and after two weeks, 30 $\mu$g of human VSGF was administered to them at once a week, four frequencies in total. Blood was collected from a venous plexus on eyegrounds, its serum antibody titer was tested by enzyme immunoassay method described below, and a spleen was dissected from a mouse which showed enough antibody titer after three days of the final immunization.

The spleen was chopped in MEM culture medium (Nissui Seiyaku Co.), taken into pieces with a pair of tweezers, centrifuged at 12000 rpm for 5 min, treated with tris-ammonium chloride buffer solution (pH 7.65) for 1–2 min. to remove erythrocytes after the supernatant was discarded, and finally washed with the MEM culture medium three times, which was used for cell fusion.

(2) Enzyme immunoassay

The purified human VSGF (10 $\mu$g/ml) was poured into a 96-well plate for EIA (Greiner Co.) in an amount of 50 $\mu$l/well, and it was left at 4° C. overnight to coat the antigen over the plate. Then, PBS solution containing 1% BSA (BSA-PBS) was poured thereto in an amount of 100 $\mu$l/well, and it was left at room temperature for 1 hour to block residues bound to a protein remained on the plate. Then, BSA-PBS in the wells were discarded, the wells were washed well with the PBS. Samples (mouse serum, supernatant of hybridoma culture, and purified monoclonal antibody) prepared by diluting with BSA-PBS were poured into the well in an amount of 50 $\mu$l/well as the first antibody, and it was left for 2 hours. After washing with PBS or PBS-Tween, peroxidase-labeled anti-rat immunoglobulin antibody (DAKO Co.) was poured into the well in an amount of 50 $\mu$l/well as the second antibody, and it was left at room temperature for 1 hour.

After washing with PBS-Tween, color development was carried out by using ABTS solution [a solution obtained by dissolving 550 mg of 2,2'-azino-bis(3-ethylbenzothiazolin-6-sulfonic acid)2 ammonium in 1 liter of 0.1 M citric acid buffer solution (pH 4.2) and adding 1 $\mu$l/ml hydrogen peroxide thereto just before the use] and absorbance was measured at OD415 nm.

(3) Preparation of mouse myeloma cells

A myeloma cell line P3-U1 of 8-azaguanine resistant mouse was cultivated in a normal medium, and more than $2 \times 10^7$ cells were reserved for cell fusion and the cells were used as parent for cell fusion.

(4) Preparation of hybridoma

Spleen cells of rat or mouse obtained in (1) and myeloma cells obtained in (3) were mixed together at the ratio of 10:1, and the mixture was centrifuged at 1200 rpm for 5 min. The supernatant was discarded, sedimented cell groups were taken into pieces, 0.2–1 ml of mixed solution containing 2 g of polyethylene glycol 1000 (PEG-1, 1000), 2 ml of MEM culture medium, and 0.7 ml of dimethyl sulfoxide was added to $10^8$ rat or mouse spleen cells with stirring at 37° C., and 1–2 ml of the MEM medium was added thereto every 1–2 min., several times, and the MEM medium was added to make the total volume 50 ml. After centrifugation (900 rpm, 5 min.), supernatant was discarded, cell groups were taken into pieces mildly, and finally, cells were suspended in 100 ml of HAT medium by mild sucking-in and -out with a pipette.

The suspension was poured in a 96-well culture plate in an amount of 100 $\mu$l/well, and it was cultivated in a 5% $CO_2$ incubator at 37° C. for 10–14 days under 5% $CO_2$. The supernatant of the culture was examined by the enzyme immunoassay described in (2) to select wells reacting with human VS GF, and culture medium was changed to HT medium and normal medium, and then, cloning were repeated twice to establish an anti-human VSGF monoclonal antibody-forming hybridoma.

(5) Purification of monoclonal antibody

The hybridoma obtained in (4) was injected in an abdominal cavity of 8-week old female nude mouse (Balb/c) which had been treated with pristanic acid in an amount of 5–20× $10^6$ cells/each animal. After 10–21 days from the treatment, the hybridoma was formed into ascites tumors. Ascites was collected from a mouse having much ascites (1–8 ml/animal) and centrifuged (3000 rpm, 5 min) to remove solid. When the monoclonal antibody is IgM, the purified monoclonal antibody was obtained by salting-out with 50% ammonium sulfate, dialysis with PBS to which 0.5 M sodium chloride was added, passing through a column of Cellulofine GSL2000 (Seikagaku Kougyou Co.; bed volume 750 ml) at flow rate of 15 ml/h, and collecting IgM fraction.

When the monoclonal antibody was IgG, the monoclonal antibody was purified by caprylic acid precipitation method [Antibodies: a Laboratory Manual. Cold Spring Harbor Laboratory, (1988)].

Subclasses of antibody were identified by enzyme immunoassay using a subclass typing kit.

Example 9
Inhibiting Activity of VSGF Against Vascular Formation

Figure 8A:
FIG. 8A and FIG. 8B show diagrams of the tissue of rat cornea.
Figure 8B:

Inhibiting activity of recombinant human VSGF against vascular formation induced by basic fibroblast growth factor (bFGF) of rat cornea was measured by the method described in literature [Cell, 56, 345 (1989)]. VSGF and bFGF were dissolved in 5 µl of PBS, mixed with 5 µl of 12% ethanol solution of methyl methacrylate (Sigma Co.) to form gel, which was injected to a cornea of a rat. FIG. 8A and FIG. 8B show the tissue diagram of the cornea after three days from the experiment.

The present invention provides a novel vascular smooth muscle cell growth factor. The factor of the present invention promotes the vascular smooth muscle cell growth and is effective on wound healing. Further, the factor inhibits the vascular formation activity of fibroblast growth factor and is effective on therapy of abnormal vascular formation, and therefore, the present invention provides a wound healing agent containing the factor of the present invention and an agent against abnormal vascular formation, containing the factor. Furthermore, the present invention provides an antibody recognizing the factor and also provides a diagnostic method of pathology to which the factor relates.

What is claimed is:

1. An isolated polypeptide having an amino acid sequence represented by SEQ ID NO:1 or SEQ ID NO: 3.

2. A composition for healing wounds, containing an isolated polypeptide having an amino acid sequence represented by SEQ ID NOs: 1 or 3.

3. A composition for inhibiting formation of a blood vessel, the composition containing an isolated polypeptide having an amino acid sequence represented by SEQ ID NOs: 1 or 3.

* * * * *

SEQUENCE LISTING

<160> NUMBER OF SEQ ID NOS: 21

<210> SEQ ID NO 1
<211> LENGTH: 807
<212> TYPE: PRT
<213> ORGANISM: human

<400> SEQUENCE: 1

Met Arg Leu Ser Pro Ala Pro Leu Lys Leu Ser Arg Thr Pro Ala Leu
 1               5                  10                  15

Leu Ala Leu Ala Leu Pro Leu Ala Ala Ala Leu Ala Phe Ser Asp Glu
                20                  25                  30

Thr Leu Asp Lys Val Pro Lys Ser Glu Gly Tyr Cys Ser Arg Ile Leu
            35                  40                  45

Arg Ala Gln Gly Thr Arg Arg Glu Gly Tyr Thr Glu Phe Ser Leu Arg
        50                  55                  60

Val Glu Gly Asp Pro Asp Phe Tyr Lys Pro Gly Thr Ser Tyr Arg Val
65                  70                  75                  80

Thr Leu Ser Ala Ala Pro Pro Ser Tyr Phe Arg Gly Phe Thr Leu Ile
                85                  90                  95

Ala Leu Arg Glu Asn Arg Glu Gly Asp Lys Glu Glu Asp His Ala Gly
            100                 105                 110

Thr Phe Gln Ile Ile Asp Glu Glu Glu Thr Gln Phe Met Ser Asn Cys
        115                 120                 125

Pro Val Ala Val Thr Glu Ser Thr Pro Arg Arg Arg Thr Arg Ile Gln
    130                 135                 140

Val Phe Trp Ile Ala Pro Pro Ala Gly Thr Gly Cys Val Ile Leu Lys
145                 150                 155                 160

Ala Ser Ile Val Gln Lys Arg Ile Ile Tyr Phe Gln Asp Glu Gly Ser
                165                 170                 175

Leu Thr Lys Lys Leu Cys Glu Gln Asp Ser Thr Phe Asp Gly Val Thr
            180                 185                 190

Asp Lys Pro Ile Leu Asp Cys Cys Ala Cys Gly Thr Ala Lys Tyr Arg
        195                 200                 205

Leu Thr Phe Tyr Gly Asn Trp Ser Glu Lys Thr His Pro Lys Asp Tyr
    210                 215                 220

Pro Arg Arg Ala Asn His Trp Ser Ala Ile Ile Gly Gly Ser His Ser
225                 230                 235                 240

-continued

```
Lys Asn Tyr Val Leu Trp Glu Tyr Gly Gly Tyr Ala Ser Glu Gly Val
                245                 250                 255

Lys Gln Val Ala Glu Leu Gly Ser Pro Val Lys Met Glu Glu Glu Ile
            260                 265                 270

Arg Gln Gln Ser Asp Glu Val Leu Thr Val Ile Lys Ala Lys Ala Gln
            275                 280                 285

Trp Pro Ala Trp Gln Pro Leu Asn Val Arg Ala Ala Pro Ser Ala Glu
        290                 295                 300

Phe Ser Val Asp Arg Thr Arg His Leu Met Ser Phe Leu Thr Met Met
305                 310                 315                 320

Gly Pro Ser Pro Asp Trp Asn Val Gly Leu Ser Ala Glu Asp Leu Cys
                325                 330                 335

Thr Lys Glu Cys Gly Trp Val Gln Lys Val Val Gln Asp Leu Ile Pro
            340                 345                 350

Trp Asp Ala Gly Thr Asp Ser Gly Val Thr Tyr Glu Ser Pro Asn Lys
        355                 360                 365

Pro Thr Ile Pro Gln Glu Lys Ile Arg Pro Leu Thr Ser Leu Asp His
    370                 375                 380

Pro Gln Ser Pro Phe Tyr Asp Pro Glu Gly Gly Ser Ile Thr Gln Val
385                 390                 395                 400

Ala Arg Val Val Ile Glu Arg Ile Ala Arg Lys Gly Glu Gln Cys Asn
                405                 410                 415

Ile Val Pro Asp Asn Val Asp Asp Ile Val Ala Asp Leu Ala Pro Glu
            420                 425                 430

Glu Lys Asp Glu Asp Thr Pro Glu Thr Cys Ile Tyr Ser Asn Trp
        435                 440                 445

Ser Pro Trp Ser Ala Cys Ser Ser Thr Cys Asp Lys Gly Lys Arg
    450                 455                 460

Met Arg Gln Arg Met Leu Lys Ala Gln Leu Asp Leu Ser Val Pro Cys
465                 470                 475                 480

Pro Asp Thr Gln Asp Phe Gln Pro Cys Met Gly Pro Gly Cys Ser Asp
            485                 490                 495

Glu Asp Gly Ser Thr Cys Thr Met Ser Glu Trp Ile Thr Trp Ser Pro
        500                 505                 510

Cys Ser Ile Ser Cys Gly Met Gly Met Arg Ser Arg Glu Arg Tyr Val
    515                 520                 525

Lys Gln Phe Pro Glu Asp Gly Ser Val Cys Thr Leu Pro Thr Glu Glu
        530                 535                 540

Met Glu Lys Cys Thr Val Asn Glu Glu Cys Ser Pro Ser Ser Cys Leu
545                 550                 555                 560

Met Thr Glu Trp Gly Glu Trp Asp Glu Cys Ser Ala Thr Cys Gly Met
                565                 570                 575

Gly Met Lys Lys Arg His Arg Met Ile Lys Met Asn Pro Ala Asp Gly
            580                 585                 590

Ser Met Cys Lys Ala Glu Thr Ser Gln Ala Glu Lys Cys Met Met Pro
        595                 600                 605

Glu Cys His Thr Ile Pro Cys Leu Leu Ser Pro Trp Ser Glu Trp Ser
    610                 615                 620

Asp Cys Ser Val Thr Cys Gly Lys Gly Met Arg Thr Arg Gln Arg Met
625                 630                 635                 640

Leu Lys Ser Leu Ala Glu Leu Gly Asp Cys Asn Glu Asp Leu Glu Gln
                645                 650                 655
```

```
Val Glu Lys Cys Met Leu Pro Glu Cys Pro Ile Asp Cys Glu Leu Thr
        660                 665                 670

Glu Trp Ser Gln Trp Ser Glu Cys Asn Lys Ser Cys Gly Lys Gly His
        675                 680                 685

Val Ile Arg Thr Arg Met Ile Gln Met Glu Pro Gln Phe Gly Gly Ala
        690                 695                 700

Pro Cys Pro Glu Thr Val Gln Arg Lys Cys Arg Ile Arg Lys Cys
705                 710                 715                 720

Leu Arg Asn Pro Ser Ile Gln Lys Pro Arg Trp Arg Glu Ala Arg Glu
                725                 730                 735

Ser Arg Arg Ser Glu Gln Leu Lys Glu Ser Glu Gly Glu Gln Phe
        740                 745                 750

Pro Gly Cys Arg Met Arg Pro Trp Thr Ala Trp Ser Glu Cys Thr Lys
        755                 760                 765

Leu Cys Gly Gly Gly Ile Gln Glu Arg Tyr Met Thr Val Lys Lys Arg
        770                 775                 780

Phe Lys Ser Ser Gln Phe Thr Ser Cys Lys Asp Lys Lys Glu Ile Arg
785                 790                 795                 800

Ala Cys Asn Val His Pro Cys
                805

<210> SEQ ID NO 2
<211> LENGTH: 3079
<212> TYPE: DNA
<213> ORGANISM: human

<400> SEQUENCE: 2
ggcacaaagt tgggggccgc gaagatgagg ctgtccccgg cgccctgaa gctgagccgg      60 actccggcac tgctggccct ggcgctgccc ctggccgcgg cgctggcctt ctccgacgag     120
accctggaca aagtgcccaa gtcagagggc tactgtagcc gtatcctgcg cgcccagggc     180
acgcggcgcg agggctacac cgagttcagc ctccgcgtgg agggcgaccc cgacttctac     240
aagccgggaa ccagctaccg cgtaacactt tcagctgctc ctccctccta cttcaggaga     300
ttcacattaa ttgccctcag agaacagaga gagggtgata aggaagaaga ccatgctggg     360
accttccaga tcatagacga agaagaaact cagtttatga caattgccc tgttgcagtc     420 actgaaagca ctccacggag gaggacccgg atccaggtgt tttggatagc caccagcg      480 ggaacaggct gcgtgattct gaaggccagc atcgtacaaa aacgcattat ttatttttcaa    540 gatgagggct ctctgaccaa gaaactttgt gaacaagatt ccacatttga tggggtgact    600
gacaaaccca tcttagactg ctgtgcctgc ggaactgcca gtacagact cacatttttat    660 gggaattggt ccgagaagac acacccaaag gattaccctc gtcgggccaa ccactggtct    720
gcgatcatcg gaggatccca ctccaagaat tatgtactgt gggaatatgg aggatatgcc    780
agcgaaggcg tcaaacaagt tgcagaattg ggctcacccg tgaaaatgga ggaagaaatt    840
cgacaacaga gtgatgaggt cctcaccgtc atcaaagcca agcccaatg gccagcctgg    900 cagcctctca acgtgagagc agcaccttca gctgaatttt ccgtggacag aacgcgccat    960
ttaatgtcct tcctgaccat gatgggccct agtcccgact ggaacgtagg cttatctgca   1020
gaagatctgt gcaccaagga atgtggctgg gtccagaagg tggtgcaaga cctgattccc   1080
tgggacgctg gcaccgacag cggggtgacc tatgagtcac ccaacaaacc caccattccc   1140
caggagaaaa tccggcccct gaccagcctg accatcctc agagtccttt ctatgaccca   1200
gagggtgggt ccatcactca gtagccaga gttgtcatcg agagaatcgc acggaagggt   1260
```

```
gaacaatgca atattgtacc tgacaatgtc gatgatattg tagctgacct ggctccagaa   1320
gagaaagatg aagatgacac ccctgaaacc tgcatctact ccaactggtc cccatggtcc   1380
gcctgcagct cctccacctg tgacaaaggc aagaggatgc gacagcgcat gctgaaagca   1440
cagctggacc tcagcgtccc ctgccctgac acccaggact tccagccctg catgggccct   1500
ggctgcagtg acgaagacgg ctccacctgc accatgtccg agtggatcac ctggtcgccc   1560
tgcagcatct cctgcggcat gggcatgagg tcccgggaga ggtatgtgaa gcagttcccg   1620
gaggacggct ccgtgtgcac gctgcccact gaggaaatgg agaagtgcac ggtcaacgag   1680
gagtgctctc ccagcagctg cctgatgacc gagtggggcg agtgggacga gtgcagcgcc   1740
acctgcggca tgggcatgaa gaagcggcac cgcatgatca gatgaacccc gcagatggc    1800 tccatgtgca agccgagac atcacaggca gagaagtgca tgatgccaga gtgccacacc    1860
atcccatgct tgctgtcccc atggtccgag tggagtgact gcagcgtgac ctgcgggaag   1920
ggcatgcgaa cccgacagcg gatgctcaag tctctggcag aacttggaga ctgcaatgag   1980
gatctggagc aggtggagaa gtgcatgctc cctgaatgcc ccattgactg tgagctcacc   2040
gagtggtccc agtggtcgga atgtaacaag tcatgtggga aggccacgt gattcgaacc    2100 cggatgatcc aaatggagcc tcagtttgga ggtgcaccct gcccagagac tgtgcagcga   2160
aaaaagtgcc gcatccgaaa atgccttcga aatccatcca tccaaaagcc acgctggagg   2220
gaggcccgag agagccggcg gagtgagcag ctgaaggaag agtctgaagg ggagcagttc   2280
ccaggttgta ggatgcgccc atggacggcc tggtcagaat gcaccaaact gtgcggaggt   2340
ggaattcagg aacgttacat gactgtaaag aagagattca aaagctccca gtttaccagc   2400
tgcaaagaca agaaggagat cagagcatgc aatgttcatc cttgttagca agggtacgag   2460
ttccccaggg ctgcactcta gattccgagt caccaatgg ctggattatt tgcttgttta    2520
agacaattta aattgtgtac gctagttttc atttttgcag tgtggttcgc ccagtagtct   2580
tgtggatgcc agagacatcc tttctgaata cttcttgatg ggtacaggct gagtggggcg   2640
ccctcacctc cagccagcct cttcctgcag aggagtagtg tcagccacct tgtactaagc   2700
tgaaacatgt ccctctggag cttccacctg gccaggagg acggagactt tgacctactc    2760
cacatggaga ggcaaccatg tctggaagtg actatgcctg agtcccaggg tgcggcaggt   2820
aggaaacatt cacagatgaa gacagcagat tccccacatt ctcatctttg gcctgttcaa   2880
tgaaaccatt gtttgcccat ctcttcttag tggaacttta ggtctctttt caagtctcct   2940
cagtcatcaa tagttcctgg ggaaaaacag agctggtaga cttgaagagg agcattgatg   3000
ttgggtggct tttgttcttt cactgagaaa ttcggaatac atttgtctca cccctgatat   3060
tggttcctga tgccccagc                                                3079
```

<210> SEQ ID NO 3
<211> LENGTH: 807
<212> TYPE: PRT
<213> ORGANISM: BOVINE

<400> SEQUENCE: 3

Met Arg Leu Ser Pro Val Leu Leu Arg Leu Ser Arg Gly Pro Ala Leu
 1               5                   10                  15

Leu Ala Leu Ala Leu Pro Leu Ala Val Ala Leu Ala Phe Ser Asp Glu
                20                  25                  30

Thr Leu Asp Lys Val Pro Lys Ser Glu Gly Tyr Cys Ser Arg Ile Leu
            35                  40                  45

```
Arg Val Gln Gly Thr Arg Arg Glu Gly Tyr Thr Glu Phe Ser Leu Arg
     50                      55                      60
Val Glu Gly Asp Pro Asp Phe Tyr Lys Pro Gly Thr Ser Tyr Arg Val
 65                      70                      75              80
Thr Leu Ser Ala Ala Pro Pro Ser Tyr Phe Arg Gly Phe Thr Leu Ile
                     85                      90                  95
Ala Leu Lys Glu Asn Arg Glu Gly Asp Lys Glu Asp His Ala Gly
                100                     105             110
Thr Phe Gln Ile Ile Asp Glu Glu Thr Gln Phe Met Ser Asn Cys
            115                     120                 125
Pro Val Ala Val Thr Glu Ser Thr Pro Arg Arg Thr Arg Ile Gln
    130                     135                 140
Val Phe Trp Ile Ala Pro Pro Ala Gly Thr Gly Cys Val Ile Leu Lys
145                     150                     155             160
Ala Ser Ile Val Gln Lys Arg Ile Ile Tyr Phe Gln Asp Glu Gly Ser
                165                     170                 175
Leu Thr Lys Lys Leu Cys Glu Gln Asp Ser Thr Phe Asp Gly Val Thr
                180                     185                 190
Asp Lys Pro Ile Leu Asp Cys Cys Ala Cys Gly Thr Ala Lys Tyr Arg
            195                     200                 205
Leu Thr Phe Tyr Gly Asn Trp Ser Glu Lys Thr His Pro Lys Asp Tyr
    210                     215                 220
Pro Arg Arg Ala Asn His Trp Ser Ala Ile Ile Gly Gly Ser His Ser
225                     230                     235             240
Lys Asn Tyr Val Leu Trp Glu Tyr Gly Gly Tyr Ala Ser Glu Gly Val
                245                     250                 255
Lys Gln Val Ala Glu Leu Gly Ser Pro Val Lys Met Glu Glu Glu Ile
                260                     265                 270
Arg Gln Gln Ser Asp Glu Val Leu Thr Val Ile Lys Ala Lys Ala Gln
            275                     280                 285
Trp Pro Ala Trp Gln Pro Leu Asn Val Arg Ala Ala Pro Ser Ala Glu
    290                     295                 300
Phe Ser Val Asp Arg Thr Arg His Leu Met Ser Phe Leu Thr Met Met
305                     310                 315                 320
Gly Pro Ser Pro Asp Trp Asn Val Gly Leu Ser Ala Glu Asp Leu Cys
                325                     330                 335
Thr Lys Glu Cys Gly Trp Val Gln Lys Val Val Gln Asp Leu Ile Pro
            340                     345                 350
Trp Asp Ala Gly Thr Asp Ser Gly Val Thr Tyr Glu Ser Pro Asn Lys
    355                     360                 365
Pro Thr Ile Pro Gln Glu Lys Ile Arg Pro Leu Thr Ser Leu Asp His
    370                     375                 380
Pro Gln Ser Pro Phe Tyr Asp Pro Glu Gly Gly Ser Ile Thr Gln Val
385                     390                     395             400
Ala Arg Val Val Ile Glu Arg Ile Ala Arg Lys Gly Glu Gln Cys Asn
                405                     410                 415
Ile Val Pro Asp Asn Val Asp Ile Val Ala Asp Leu Ala Pro Glu
            420                     425                 430
Glu Lys Asp Glu Asp Thr Pro Glu Thr Cys Ile Tyr Ser Asn Trp
        435                     440                 445
Ser Pro Trp Ser Ala Cys Ser Ser Thr Cys Asp Lys Gly Lys Arg
    450                     455                 460
```

Met Arg Gln Arg Met Leu Lys Ala Gln Leu Asp Leu Ser Val Pro Cys
465                 470                 475                 480

Pro Asp Thr Gln Asp Phe Gln Pro Cys Met Gly Pro Gly Cys Ser Asp
            485                 490                 495

Glu Asp Gly Ser Thr Cys Thr Met Ser Glu Trp Ile Thr Trp Ser Pro
            500                 505                 510

Cys Ser Ile Ser Cys Gly Thr Gly Thr Arg Ser Arg Glu Arg Tyr Val
            515                 520                 525

Lys Gln Phe Pro Glu Asp Gly Ser Val Cys Thr Leu Pro Thr Glu Glu
            530                 535                 540

Thr Glu Lys Cys Thr Val Asn Glu Glu Cys Ser Pro Ser Ser Cys Leu
545                 550                 555                 560

Thr Thr Glu Trp Gly Glu Trp Asp Glu Cys Ser Ala Thr Cys Gly Met
                565                 570                 575

Gly Met Lys Lys Arg His Arg Met Val Lys Met Ser Pro Ala Asp Gly
            580                 585                 590

Ser Met Cys Lys Ala Glu Thr Ser Gln Ala Glu Lys Cys Met Met Pro
            595                 600                 605

Glu Cys His Thr Ile Pro Cys Leu Leu Ser Leu Trp Ser Glu Trp Ser
610                 615                 620

Asp Cys Ser Val Thr Cys Gly Lys Gly Met Arg Thr Arg Gln Arg Met
625                 630                 635                 640

Leu Lys Ser Leu Ala Glu Leu Gly Asp Cys Asn Glu Glu Leu Glu Gln
                645                 650                 655

Val Glu Lys Cys Met Leu Pro Glu Cys Pro Ile Asp Cys Glu Leu Thr
            660                 665                 670

Glu Trp Ser Gln Trp Ser Glu Cys Asn Lys Ser Cys Gly Lys Gly His
            675                 680                 685

Met Ile Arg Thr Arg Met Ile Gln Met Glu Pro Gln Phe Gly Gly Thr
            690                 695                 700

Pro Cys Pro Glu Thr Val Gln Arg Lys Lys Cys Arg Ile Arg Lys Cys
705                 710                 715                 720

Leu Arg Asn Pro Ser Ile Gln Asn Leu Arg Trp Arg Glu Ala Arg Glu
                725                 730                 735

Ser Arg Arg Ser Glu Gln Leu Arg Glu Glu Ser Asp Gly Asp Gln Phe
            740                 745                 750

Pro Gly Cys Arg Met Arg Pro Trp Thr Ala Trp Ser Glu Cys Thr Lys
            755                 760                 765

Leu Cys Gly Gly Gly Ile Gln Glu Arg Tyr Met Thr Val Lys Lys Arg
770                 775                 780

Phe Lys Ser Ser Gln Phe Thr Ser Cys Lys Asp Lys Lys Glu Ile Arg
785                 790                 795                 800

Ala Cys Asn Val His Pro Cys
            805

<210> SEQ ID NO 4
<211> LENGTH: 4061
<212> TYPE: DNA
<213> ORGANISM: BOVINE

<400> SEQUENCE: 4
ccagcaccgg ctcggagctc cgctcccgcc tgggctctgc caggtctcgt ttccgcgggg    60 acccttcgg gcaggagtcg tgcggcgaga gcagcggcca gggcacaaag ttgggggccc   120
gcgaggatga ggctgtcccc ggtgctcctg aggctgagcc gggtccagc gctgctggcc   180

-continued

```
ctggcgctgc ccctggcggt ggcgctggcc ttctccgacg agaccctgga caaagtgccc      240
aagtcagagg gctactgcag ccgcatcctg cgcgtccagg gcacgcggcg tgagggctac      300
accgagttca gcctccgcgt ggagggcgac cccgacttct ataagccggg aaccagctac      360
cgcgtgacgc tttcagctgc ccctcccctcc tatttcagag gattcacctt aatcgccctc     420
aaagaaaaca gagagggtga taaagaggaa gaccatgctg ggaccttcca gatcatagat      480
gaagaagaaa cacagtttat gagtaattgc cccgttgcgg tcacagaaag caccccacgg      540
aggcggacgc ggatccaggt gttctggata gcgccacctg caggaactgg ctgcgtaatt      600
ctaaaggcta gcattgtaca gaaacgcatc atttattttc aagatgaagg ctctctgacc      660
aagaaacttt gtgaacaaga ttccacattt gatgggtga ctgacaaacc aatcctagac       720
tgctgcgcct gtgggactgc taagtacagg ctcacatttt atgggaactg gtctgagaag      780
acacacccaa aggattaccc tcgtcgggcc aatcactggt ctgcaatcat cggcggatcc      840
cactccaaga attacgtgct gtgggagtat ggaggatatg caagcgaagg cgtcaaacag      900
gttgcagaat tgggctctcc agtgaaaatg gaggaggaaa ttcgacaaca gagcgacgag      960
gtcctcaccg tcatcaaagc caaagctcag tggccagcct ggcagcctct caatgtgaga     1020
gcagcaccct cggctgaatt ttcagtggac aggacgcgcc acttgatgtc cttcctgacc     1080
atgatgggcc ccagccccga ctggaacgtg ggcctgtccg cagaggatct gtgcaccaaa     1140
gagtgcggct gggtccagaa ggtggtgcag gacctgattc cctgggacgc gggcaccgac     1200
agcggggtga cctatgagtc acccaacaag cccacaattc cccaggagaa aatccgaccc     1260
ctgaccagtc tggaccatcc tcagagtcct ttttatgatc cagagggtgg atccatcact     1320
caagtagcca gagttgtcat cgagagaatc gcccggaagg gggaacagtg caatattgtg     1380
cccgacaatg tcgacgatat tgtagcagac ctggctccag aagagaaaga tgaagatgac     1440
acccctgaaa cctgcatcta ctccaactgg tccccgtggt ccgcctgcag ctcctccacc     1500
tgcgacaaag caagaggat gcggcagcgc atgctgaagg cacagctgga cctcagcgtc     1560
ccctgccccg acacccagga cttccagccc tgcatgggcc ccggctgcag cgacgaagac     1620
ggctccacgt gcaccatgtc cgagtggatc acctggtcgc cctgcagcat ctcctgcggc     1680
accggcacgc ggtcccggga gaggtacgtg aagcagttcc cagaggacgg ctccgtgtgc     1740
acgctgccca ccgaggagac agagaagtgc acggtcaacg aagagtgctc tcccagcagc     1800
tgcctgacga ccgagtgggg cgagtgggac gagtgcagcg ccacctgcgg gatgggcatg     1860
aagaagcggc accgcatggt caagatgagc cccgcggacg gctccatgtg caaggctgaa     1920
acatctcagg cagagaagtg catgatgccc gagtgccaca ccatcccatg cttgctatcc     1980
ctgtggtctg agtggagtga ctgcagcgtg acctgtggga agggcatgcg gacccgccag     2040
cggatgctca agtctctagc cgaactcggg gactgtaatg aggagctgga gcaggtggag     2100
aagtgcatgc tgcctgaatg ccccattgac tgtgagctca cggagtggtc ccagtggtcg     2160
gaatgtaaca agtcatgtgg gaaggacac atgattcgaa cccgcatgat ccaaatggag      2220
cctcagtttg gaggcacacc ctgcccagag actgtacagc ggaaaaagtg ccgcatccgg     2280
aaaatgcctc cgaaatccatc catccagaac ctgcgctgga gggaggcccg agagagccgg    2340
aggagtgaac agctgaggga ggagtcggac ggggaccagt ttccaggctg caggatgcgc     2400
ccttggacag cctggtcaga atgcaccaaa ctgtgcggag gagggatcca ggaacgctac     2460
atgactgtga agaagaggtt caaaagctcc cagtttacca gctgcaaaga caagaaggag     2520
```

-continued

```
atcagagcgt gcaacgtcca tccgtgttaa ccagggtaca cgtgtcccag ggctgcactc   2580
tagaccccca gaggcaatgg ctggatcgtt tgtttgcttg tttaaggcag tttcaattgt   2640
gtacactagt tttcatttct gcagggggt ccgcccagta gtcctgtgga tgctacggcc    2700
acccttctgt acacttcttg gtgggcacag actgggggtg ggggcatggg gctccctcat   2760
ccttagccgg ccctcctcca gcacaagtga gtagtgccag tcacctgtgc tgaacagaac   2820
gtgtccctct caagcatcca cctgggcggc aggacagaga ccctggcttc cccaacatgg   2880
agaggcagct gtgcccgcag ctgaccctgt gcatcggtgc cagggcgcag cagcagggag   2940
actttcctga ttgggtggga atgagagcag agtcccctca ttcttgcctg tggcctgctt   3000
gctcttgcag caaactactg tttgcttgtc tcttctcatt tagtggaact ttagggtccc   3060
ttgttgagtc tcctcagtca tcaacagttc ttggggaaac agctggcaaa catgaagaga   3120
agcactgatg ttgggtggct tttcttcttt cactgagaaa ttctgaatcc agtatctcaa   3180
cccgatactc caaaggaaaa aaatgatggc tgcttttta aaaaaatata accagttctt    3240
acacctgagg taaacatac tgggtctaga aattattatt cccttctttt ggttttttt     3300 ggatataatt ctcttaggaa gccagcctta ggaaccttgt gatcctagat ccttactaga   3360
accacagcag caaaattggc ctctagagca gtcccaggct tgagtttttt taaaccttcc   3420
aacacagact tttaaatcag caaaccagtt tctaacaaga aaaccttttt ttcagttatg   3480
caaacattct gccgagtttg tctgcagtcc accaagccat tccttcaaca aaatactat    3540 cttagaactt gaaagggttt ttacagtcat aaaatttat atgtagagag aaaaagtgtt    3600
tcagagacca agacaaatcc agggagaaag gaatgtcaca gaatcaagtt agcagaaaaa   3660
tctggtggga agtcaaacgt acatacatca gccctccaca ccaagggtct ggtcctctga   3720
caccaccaca gggagggtca tggttttccg ttccttcca cacacaagca caccaaattc    3780
agggagactg actaccaagg attagtgtaa aaggacgttt taccaacttg agtccatcag   3840
cagtttctac tcactcattt actgttaaaa tcactgttct gctcttgttg caggccttct   3900
ttatcgtgct taatccaaat atgtaccatg gatgagatgc atacaatgct ttgaatacac   3960
tactttaaga atttgcattg aatacttcag gatattccaa acacaacatt atatatat     4020 atatatatgc tacagccttg aatctgtact gttttaacta c                       4061
```

<210> SEQ ID NO 5
<211> LENGTH: 807
<212> TYPE: PRT
<213> ORGANISM: RAT

<400> SEQUENCE: 5

```
Met Arg Leu Ser Pro Ala Pro Leu Arg Leu Ser Arg Gly Pro Ala Leu
 1               5                  10                  15

Leu Ala Leu Ala Leu Pro Leu Ala Ala Ala Leu Ala Phe Ser Asp Glu
            20                  25                  30

Thr Leu Asp Lys Val Ala Lys Ser Glu Gly Tyr Cys Ser Arg Ile Leu
        35                  40                  45

Arg Ala Gln Gly Thr Arg Arg Glu Gly Tyr Thr Glu Phe Ser Leu Arg
    50                  55                  60

Val Glu Gly Asp Pro Asp Phe Tyr Lys Pro Gly Ser Ser Tyr Arg Val
65                  70                  75                  80

Thr Leu Ser Ala Ala Pro Pro Ser Tyr Phe Arg Gly Phe Thr Leu Ile
                85                  90                  95

Ala Leu Lys Glu Asn Arg Glu Gly Asp Lys Glu Glu Asp His Ala Gly
```

-continued

```
               100                 105                 110
Thr Phe Gln Ile Ile Asp Glu Glu Thr Gln Phe Met Ser Asn Cys
            115                 120                 125
Pro Val Ala Val Thr Glu Ser Thr Pro Arg Arg Thr Arg Ile Gln
130                 135                 140
Val Phe Trp Ile Ala Pro Pro Thr Gly Thr Gly Cys Val Ile Leu Lys
145                 150                 155                 160
Ala Ser Ile Val Gln Lys Arg Ile Ile Tyr Phe Gln Asp Glu Gly Ser
            165                 170                 175
Leu Thr Lys Lys Leu Cys Glu Gln Asp Pro Thr Leu Asp Gly Val Thr
            180                 185                 190
Asp Arg Pro Ile Leu Asp Cys Cys Ala Cys Gly Thr Ala Lys Tyr Arg
            195                 200                 205
Leu Thr Phe Tyr Gly Asn Trp Ser Glu Lys Thr His Pro Lys Asp Tyr
            210                 215                 220
Pro Arg Arg Ala Asn His Trp Ser Ala Ile Ile Gly Gly Ser His Ser
225                 230                 235                 240
Lys Asn Tyr Val Leu Trp Glu Tyr Gly Gly Tyr Ala Ser Glu Gly Val
            245                 250                 255
Lys Gln Val Ala Glu Leu Gly Ser Pro Val Lys Met Glu Glu Ile
            260                 265                 270
Arg Gln Gln Ser Asp Glu Val Leu Thr Val Ile Lys Ala Lys Ala Gln
            275                 280                 285
Trp Pro Ser Trp Gln Pro Val Asn Val Arg Ala Ala Pro Ser Ala Glu
            290                 295                 300
Phe Ser Val Asp Arg Thr Arg His Leu Met Ser Phe Leu Thr Met Met
305                 310                 315                 320
Gly Pro Ser Pro Asp Trp Asn Val Gly Leu Ser Ala Glu Asp Leu Cys
            325                 330                 335
Thr Lys Glu Cys Gly Trp Val Gln Lys Val Val Gln Asp Leu Ile Pro
            340                 345                 350
Trp Asp Ala Gly Thr Asp Ser Gly Val Thr Tyr Glu Ser Pro Asn Lys
            355                 360                 365
Pro Thr Ile Pro Gln Glu Lys Ile Arg Pro Leu Thr Ser Leu Asp His
            370                 375                 380
Pro Gln Ser Pro Phe Tyr Asp Pro Glu Gly Gly Ser Ile Thr Gln Val
385                 390                 395                 400
Ala Arg Val Val Ile Glu Arg Ile Ala Arg Lys Gly Glu Gln Cys Asn
            405                 410                 415
Ile Val Pro Asp Asn Val Asp Asp Ile Val Ala Asp Leu Ala Pro Glu
            420                 425                 430
Glu Lys Asp Glu Asp Asp Thr Pro Glu Thr Cys Ile Tyr Ser Asn Trp
            435                 440                 445
Ser Pro Trp Ser Ala Cys Ser Ser Thr Cys Glu Lys Gly Lys Arg
450                 455                 460
Met Arg Gln Arg Met Leu Lys Ala Gln Leu Asp Leu Ser Val Pro Cys
465                 470                 475                 480
Pro Asp Thr Gln Asp Phe Gln Pro Cys Met Gly Pro Gly Cys Ser Asp
            485                 490                 495
Glu Asp Gly Ser Thr Cys Thr Met Ser Glu Trp Ile Thr Trp Ser Pro
            500                 505                 510
Cys Ser Val Ser Cys Gly Met Gly Met Arg Ser Arg Glu Arg Tyr Val
            515                 520                 525
```

```
Lys Gln Phe Pro Glu Asp Gly Ser Val Cys Met Leu Pro Thr Glu Glu
            530                 535                 540

Thr Glu Lys Cys Thr Val Asn Glu Glu Cys Ser Pro Ser Ser Cys Leu
545                 550                 555                 560

Val Thr Glu Trp Gly Glu Trp Asp Asp Cys Ser Ala Thr Cys Gly Met
                565                 570                 575

Gly Met Lys Lys Arg His Arg Met Val Lys Met Ser Pro Ala Asp Gly
                580                 585                 590

Ser Met Cys Lys Ala Glu Thr Ser Gln Ala Glu Lys Cys Met Met Pro
            595                 600                 605

Glu Cys His Thr Ile Pro Cys Leu Leu Ser Pro Trp Ser Glu Trp Ser
        610                 615                 620

Asp Cys Ser Val Thr Cys Gly Lys Gly Met Arg Thr Arg Gln Arg Met
625                 630                 635                 640

Leu Lys Ser Leu Ala Glu Leu Gly Asp Cys Asn Glu Asp Leu Glu Gln
                645                 650                 655

Ala Glu Lys Cys Met Leu Pro Glu Cys Pro Ile Asp Cys Glu Leu Ser
            660                 665                 670

Glu Trp Ser Gln Trp Ser Glu Cys Asn Lys Ser Cys Gly Lys Gly His
        675                 680                 685

Met Ile Arg Thr Arg Thr Ile Gln Met Glu Pro Gln Phe Gly Gly Ala
        690                 695                 700

Pro Cys Pro Glu Thr Val Gln Arg Lys Cys Arg Ala Arg Lys Cys
705                 710                 715                 720

Leu Arg Ser Pro Ser Ile Gln Lys Leu Arg Trp Arg Glu Ala Arg Glu
                725                 730                 735

Ser Arg Arg Ser Glu Gln Leu Arg Glu Glu Ser Asp Gly Glu Gln Phe
            740                 745                 750

Pro Gly Cys Arg Met Arg Pro Trp Thr Ala Trp Ser Glu Cys Thr Lys
                755                 760                 765

Leu Cys Gly Gly Gly Ile Gln Glu Arg Tyr Met Thr Val Lys Lys Arg
            770                 775                 780

Phe Lys Ser Ser Gln Phe Thr Ser Cys Lys Asp Lys Lys Glu Ile Arg
785                 790                 795                 800

Ala Cys Asn Val His Pro Cys
                805
```

<210> SEQ ID NO 6
<211> LENGTH: 4029
<212> TYPE: DNA
<213> ORGANISM: RAT

<400> SEQUENCE: 6

```
ccctccctct tcgcgctcct tcgccaccgc ccgcccctca gctccgctgc tcggctccgc    60
tcagagcagc gcagctccgc agccaaagcg aggcgggctc gggctcccca ccgccagtgc   120
cacccgggct cctccagctt tcgcctctgc agctcccgtc acttggagta aaagtgtcct   180
gacagggtc tgcaacatca gcagaaagtt gggaggtcct cgagaatgag ctatctccc    240
gcgcccctga ggcttagccg gggtccggcg ctgctggccc tggcgctgcc cctgccgca   300
gcgctcgctt tctcggatga gaccctggac aaagtggcca agtcggaggg ctactgcagc   360
cgcatcttgc gcgcccaggg cacacggcgt gagggataca cagagttcag cctccgcgtg   420
gaaggcgacc ctgacttcta taagccagga agcagctacc gagtgacact ctcggctgcc   480
```

-continued

| | | | |
|---|---|---|---|
| cctccctcct acttcagagg cttcacgtta attgctctca aagagaaccg cgaaggcgat | 540 | | |
| aaggaagaag accacgcggg caccttccag atcatagatg aagaagaaac ccagtttatg | 600 | | |
| agtaactgtc ctgtggcagt cactgaaagc acccctcgga ggaggacacg gatccaggtg | 660 | | |
| ttttggatag cgccacccac agggacaggc tgtgtgattc tgaaggccag cattgtacag | 720 | | |
| aaacgcatta tctattttca agacgagggc tccctgacca agaagctgtg tgaacaggat | 780 | | |
| cccacacttg atggagtgac ggacagaccg atcttagact gctgcgcctg cggaactgcc | 840 | | |
| aagtacagac tcacgtttta tgggaactgg tcggagaaga ctcatccaaa ggattaccct | 900 | | |
| cgtcgggcta atcactggtc tgccatcatt ggcggatccc actccaagaa ctacgtgctg | 960 | | |
| tgggagtacg gagggtatgc cagtgaaggg gtcaagcaag ttgctgaact tggctcacca | 1020 | | |
| gtaaaaatgg aggaagaaat tcgacaacag agtgatgaag tcctcactgt catcaaagcc | 1080 | | |
| aaagcccagt ggccatcctg gcagcctgtc aatgtgagag cagcaccctc agccgaattc | 1140 | | |
| tcagtggaca ggacacgcca cttgatgtcc ttcctaacca tgatgggccc cagtcctgac | 1200 | | |
| tggaacgtgg gcctatctgc agaggatctg tgcaccaagg agtgtggctg ggtccagaaa | 1260 | | |
| gtggtgcagg acctaattcc ctgggatgct ggcacggaca gcggggtgac ctacgagtca | 1320 | | |
| ccaaacaagc ccacaattcc tcaggaaaaa atccgacccc tgactagtct ggaccatcct | 1380 | | |
| cagagtcctt tctatgaccc ggaaggtggg tccatcacac aagtggccag agtcgtcatc | 1440 | | |
| gagagaattg cccggaaggg agaacaatgc aacattgtac ctgacaatgt ggatgatatt | 1500 | | |
| gtagccgacc tggctccaga agagaaagat gaagatgaca cccctgaaac ctgcatctac | 1560 | | |
| tccaactggt ccccatggtc ggcctgcagc tcttccactt gtgaaaaggg taagaggatg | 1620 | | |
| cggcaacgca tgctgaaggc acagctggac ctcagtgtcc cctgtcctga cacccaggac | 1680 | | |
| ttccagccct gcatgggccc cggctgcagc gatgaagatg ctccacctg taccatgtcg | 1740 | | |
| gagtggatca ccctggtcacc ctgcagtgtc tcgtgtggca tgggtatgag gtcccgggag | 1800 | | |
| aggtacgtga agcagttccc ggaagacggc tcggtgtgca tgctgcccac ggaagagaca | 1860 | | |
| gagaagtgca cggtcaacga ggagtgctct cctagcagct gcctggtgac tgagtgggggt | 1920 | | |
| gagtgggatg actgcagcgc cacctgtgga atgggcatga agaagcggca ccgcatggtc | 1980 | | |
| aagatgagcc ccgcggacgg ctccatgtgc aaggcggaga cttcgcaggc ggagaaatgc | 2040 | | |
| atgatgcctg agtgccatac catcccgtgc ttgctgtctc cttggtccga gtggagcgac | 2100 | | |
| tgtagcgtga cctgtgggaa gggcatgcgg acgcgccagc ggatgctcaa gtctctggca | 2160 | | |
| gagctggggg actgtaatga ggatctggag caggcggaga agtgtatgct gccagagtgc | 2220 | | |
| cccattgact gcgaactcag tgagtggtcc cagtggtctg aatgtaacaa gtcctgtggg | 2280 | | |
| aaaggtcaca tgattcgaac ccggacaatc caaatggaac ctcagtttgg aggtgcaccc | 2340 | | |
| tgcccagaga ctgtgcaacg caagaagtgc cgtgcccgga atgccttcg cagcccatcg | 2400 | | |
| atccagaagc tgcgctggag ggaggcccga gagagcagga ggagtgagca gctgagggaa | 2460 | | |
| gagtcagatg gagagcagtt ccaggctgt cggatgcgcc cgtggacagc ctggtcagag | 2520 | | |
| tgcaccaaac tgtgcggagg tgggatccaa gaacgctaca tgactgtgaa gaagaggttc | 2580 | | |
| aaaagctccc agtttaccag ctgcaaagac aagaaggaga tcagagcgtg caacgtgcac | 2640 | | |
| ccttgttagt agggggttcaa ctccccaggg ctgcattcca gattctagtc accaatggtt | 2700 | | |
| gggtggtgta tttgcttgtt taagatgatt taaattgtgt ccacatgttt tcatttttac | 2760 | | |
| cggtgtggtt tgcccaatag tcttatggag gccgaggac atcttgtctg aatacttctt | 2820 | | |
| ggtgagtaca ggccaagcgg ggcatcttgt ccccaggcgc catcttcctg cactgagttg | 2880 | | |

```
agtagtgttg gttcaccttg gtactaaact gaatcgtgtc cctctggagc atccctggt      2940 caagcagggt ggagactttg gccatccaca aggagaagca accaggatgc agcatgcggg      3000
agacacagcc attaattgca aaggacagat cctcctctct caccttggc ctgctcactc       3060 ttacagaaac ctgtttgtcc gcctccttt ttatttagca caactccagg catcttggta      3120
agtctccagg gtcatgggtt cttcggtgcc ctgaaggaga agccctgagg tgaggtggca      3180
tttgttacaa acctcccaat actgctttac tggcatcaca aggtcagcag gtgatgatgg      3240
ctacttcatt tcattgtgag ccgtgatttc cgttgagttt tgattgttgg tgccataaat      3300
gtcctaggat gctggacgga cacatcagcc ttgtcagcag atccttcttt gagccaatgt      3360
agacagtaag ctgggcactg gttccaaagc caacttaaaa tcttcctaca catatccaga     3420
ccttttttta ggttgcccaa acttccttag aataaagcat tttagctctg agaactactt      3480
gataagtctg ccaggaagcc cccaagtcaa ttcttcaaca aaaatactat cttccctact     3540 taatttttt taagtcatga tatttatag ttagaggaga gagagacaat ctattcccat        3600
gactaagaca caaacctaca agaaagggtt actcagtcaa gcctgtgcct gacttctgga     3660
ccaggcccct gattttcatg gatagtccaa aggaaggcca ggggttccca ctgactccaa     3720
gccatcagca gcacccaaac ccaggagcaa caaatattca gagaaagagg atgtttatct    3780
cagctatgag ctcattggca ggttgtactc atgcatctgt taaaagcacc accacatcct    3840
tttgcaagtc tgtttattac cgcttcatcc aaatacattt tgtggtcaag atcgacacag    3900
tgctatgaat acagtacttt aaggtctgca ttaaacacat cagaatattt cctgccacat   3960
ctatgtacaa cccctgaata tgtatttttc cttaacacaa gagagcctgt tcaattaaaa    4020
aaaaaaaaa                                                             4029
```

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
tayttycarg aygargg                                                    17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
aaratggarg argarat                                                    17

<210> SEQ ID NO 9
<211> LENGTH: 17
<212> TYPE: PRT
<213> ORGANISM: BOVINE
<220> FEATURE:
<221> NAME/KEY: "Xaa" is an unknown amino acid
<222> LOCATION: 14
<223> OTHER INFORMATION: "Xaa" is an unknown amino acid

<400> SEQUENCE: 9

Phe Ser Gln Phe Thr Leu Xaa Lys Val Pro Lys Glu Ile Xaa Ala Ser
1               5                   10                  15
Asn

<210> SEQ ID NO 10
<211> LENGTH: 10
<212> TYPE: PRT
<213> ORGANISM: BOVINE

<400> SEQUENCE: 10

Gln Val Ala Gln Leu Gly Ser Pro Val Lys
1               5                   10

<210> SEQ ID NO 11
<211> LENGTH: 13
<212> TYPE: PRT
<213> ORGANISM: BOVINE

<400> SEQUENCE: 11

Arg Ile Ile Tyr Phe Gln Asp Glu Gly Ser Leu Thr Lys
1               5                   10

<210> SEQ ID NO 12
<211> LENGTH: 19
<212> TYPE: PRT
<213> ORGANISM: BOVINE
<220> FEATURE:
<221> NAME/KEY: "Xaa" is an unknown amino acid
<222> LOCATION: 17
<223> OTHER INFORMATION: "Xaa" is an unknown amino acid

<400> SEQUENCE: 12

Asp Tyr Pro Pro Xaa Ala Asn Xaa His Ser Ala Ile Ile Gly Gly Ser
1               5                   10                  15
Xaa Ser Lys

<210> SEQ ID NO 13
<211> LENGTH: 17
<212> TYPE: PRT
<213> ORGANISM: BOVINE

<400> SEQUENCE: 13

Met Glu Glu Glu Ile Arg Gln Gln Ser Asp Glu Val Leu Thr Val Ile
1               5                   10                  15
Lys

<210> SEQ ID NO 14
<211> LENGTH: 6
<212> TYPE: PRT
<213> ORGANISM: BOVINE

<400> SEQUENCE: 14

Ala Ser Ile Val Gln Lys
1               5

<210> SEQ ID NO 15
<211> LENGTH: 25
<212> TYPE: PRT
<213> ORGANISM: BOVINE
<220> FEATURE:
<221> NAME/KEY: "Xaa" is an unknown amino acid
<222> LOCATION: 23
<223> OTHER INFORMATION: "Xaa" is an unknown amino acid

<400> SEQUENCE: 15

Ile Arg Pro Leu Thr Ser Leu Asp Asp Pro Gln Gln Pro Phe Tyr Asp
 1               5                  10                  15

Pro Glu Gly Gly Gly Ile Xaa Gln Val
            20                  25

<210> SEQ ID NO 16
<211> LENGTH: 22
<212> TYPE: PRT
<213> ORGANISM: BOVINE
<220> FEATURE:
<221> NAME/KEY: "Xaa" is an unknown amino acid
<222> LOCATION: 21
<223> OTHER INFORMATION: "Xaa" is an unknown amino acid

<400> SEQUENCE: 16

Asp Glu Asp Asp Thr Pro Glu Thr Cys Ile Tyr Ser Asn Asn Ser Pro
 1               5                  10                  15

Pro Ser Ala Ala Xaa Ser
            20

<210> SEQ ID NO 17
<211> LENGTH: 30
<212> TYPE: PRT
<213> ORGANISM: BOVINE

<400> SEQUENCE: 17

Ser Glu Gly Tyr Cys Ser Arg Ile Leu Arg Val Gln Gly Thr Arg Arg
 1               5                  10                  15

Glu Gly Tyr Thr Glu Phe Ser Leu Arg Val Glu Gly Asp Pro
            20                  25                  30

<210> SEQ ID NO 18
<211> LENGTH: 17
<212> TYPE: PRT
<213> ORGANISM: BOVINE

<400> SEQUENCE: 18

Ser Leu Ala Glu Leu Gly Asp Cys Asn Glu Glu Leu Glu Gln Val Glu
 1               5                  10                  15

Lys

<210> SEQ ID NO 19
<211> LENGTH: 23
<212> TYPE: PRT
<213> ORGANISM: BOVINE

<400> SEQUENCE: 19

Val Val Gln Asp Leu Ile Pro Trp Asp Ala Gly Thr Asp Ser Gly Val
 1               5                  10                  15

Thr Tyr Glu Ser Pro Asn Lys
            20

<210> SEQ ID NO 20
<211> LENGTH: 23
<212> TYPE: PRT
<213> ORGANISM: BOVINE

<400> SEQUENCE: 20

Gly Glu Gln Cys Asn Ile Val Pro Asp Asn Val Asp Asp Ile Val Ala
 1               5                  10                  15

Asp Leu Ala Pro Glu Glu Lys
            20

```
<210> SEQ ID NO 21
<211> LENGTH: 22
<212> TYPE: PRT
<213> ORGANISM: BOVINE
<220> FEATURE:
<221> NAME/KEY: "Xaa" is an unknown amino acid
<222> LOCATION: 18..19
<223> OTHER INFORMATION: "Xaa" is an unknown amino acid

<400> SEQUENCE: 21

Ala Gln Leu Asp Leu Ser Val Pro Gln Pro Asp Thr Gln Asp Phe Gln
 1               5                  10                  15

Pro Xaa Xaa Gly Pro Gly
            20
```